US010874718B2

(12) United States Patent
Yoo et al.

(10) Patent No.: US 10,874,718 B2
(45) Date of Patent: *Dec. 29, 2020

(54) DIRECTED STEM CELL RECRUITMENT

(71) Applicant: WAKE FOREST UNIVERSITY HEALTH SCIENCES, Winston-Salem, NC (US)

(72) Inventors: James Yoo, Winston-Salem, NC (US); Sang Jin Lee, Winston-Salem, NC (US); Anthony Atala, Winston-Salem, NC (US); Mark Van Dyke, Winston-Salem, NC (US)

(73) Assignee: WAKE FOREST UNIVERSITY HEALTH SCIENCES, Winston-Salem, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 15/640,063

(22) Filed: Jun. 30, 2017

(65) Prior Publication Data

US 2018/0140678 A1 May 24, 2018

Related U.S. Application Data

(63) Continuation of application No. 12/991,811, filed as application No. PCT/US2009/043446 on May 11, 2009, now Pat. No. 9,694,055.

(60) Provisional application No. 61/051,939, filed on May 9, 2008.

(51) Int. Cl.
| | | |
|---|---|---|
| *A61K 9/00* | (2006.01) | |
| *A61K 38/39* | (2006.01) | |
| *A61K 38/48* | (2006.01) | |
| *A61L 27/24* | (2006.01) | |
| *A61L 27/52* | (2006.01) | |
| *A61L 27/54* | (2006.01) | |

(52) U.S. Cl.
CPC ............ *A61K 38/39* (2013.01); *A61K 9/0024* (2013.01); *A61K 38/4886* (2013.01); *A61L 27/24* (2013.01); *A61L 27/52* (2013.01); *A61L 27/54* (2013.01); *A61L 2300/41* (2013.01); *A61L 2300/434* (2013.01); *A61L 2400/06* (2013.01); *A61L 2430/26* (2013.01)

(58) Field of Classification Search
CPC .. A61K 38/39; A61K 9/0024; A61K 38/4886; A61L 27/24; A61L 27/52; A61L 27/54; A61L 2300/41; A61L 2300/434; A61L 2400/06; A61L 2430/26; A61P 13/12
See application file for complete search history.

(56) References Cited

U.S. PATENT DOCUMENTS

| | | |
|---|---|---|
| 1,995,970 A | 3/1935 | Dorough |
| 2,676,945 A | 4/1954 | Higgins |
| 2,683,136 A | 7/1954 | Higgins |
| 2,703,316 A | 3/1955 | Schneider |
| 2,758,987 A | 8/1956 | Salzberg |
| 2,951,828 A | 9/1960 | Zelle et al. |
| 3,531,561 A | 9/1970 | Trehu |
| 4,251,387 A | 2/1981 | Lim et al. |
| 4,391,909 A | 7/1983 | Lim |
| 4,663,286 A | 5/1987 | Tsang et al. |
| 4,786,436 A | 11/1988 | Ogunbiyi et al. |
| 5,084,350 A | 1/1992 | Chang et al. |
| 5,227,298 A | 7/1993 | Weber et al. |
| 5,380,536 A | 1/1995 | Hubbell et al. |
| 5,451,613 A | 9/1995 | Smith et al. |
| 5,514,378 A | 5/1996 | Mikos et al. |
| 5,573,934 A | 11/1996 | Hubbell et al. |
| 5,578,314 A | 11/1996 | Cohrum et al. |
| 5,580,859 A | 12/1996 | Felgner et al. |
| 5,654,273 A | 8/1997 | Gallo et al. |
| 5,693,514 A | 12/1997 | Dorian et al. |
| 5,738,876 A | 4/1998 | Enevold |
| 5,762,959 A | 6/1998 | Soon-Shiong et al. |
| 5,787,567 A | 8/1998 | Miyazaki |
| 5,801,033 A | 9/1998 | Hubbell et al. |
| 5,846,530 A | 12/1998 | Soon-Shiong et al. |
| 5,908,777 A | 6/1999 | Lee et al. |
| 5,910,488 A | 6/1999 | Nabel et al. |
| 2004/0172061 A1* | 9/2004 | Yoshioka ................ A61L 27/38 606/215 |
| 2004/0220296 A1 | 11/2004 | Lowman et al. |
| 2006/0134050 A1* | 6/2006 | Griffith ..................... A61F 2/10 424/70.16 |
| 2006/0135912 A1 | 6/2006 | Chernomorsky et al. |
| 2006/0252981 A1 | 11/2006 | Matsuda et al. |
| 2007/0110962 A1 | 5/2007 | Tien et al. |
| 2008/0160062 A1* | 7/2008 | Richard .................. A61L 31/04 424/423 |

(Continued)

FOREIGN PATENT DOCUMENTS

WO 2000047130 A1 8/2000

OTHER PUBLICATIONS

Imasawa et al. "The potential of bone marrow-derived cells to differentiate to glomerular mesangial cells." J Am Soc Nephrol. Jul. 2001;12(7):1401-9. (Year: 2001).*

(Continued)

*Primary Examiner* — Titilayo Moloye
(74) *Attorney, Agent, or Firm* — Nelson Mullins Riley & Scarborough LLP; Thomas J. Engellenner; Reza Mollaaghababa

(57) ABSTRACT

The invention is directed to methods of inducing cell recruitment and tissue regeneration at a target site in a subject. It is also based, in part, on the discovery that a subject's own biologic resources and environmental conditions can be used for in situ tissue regeneration and thereby reduce or eliminate the need for donor cell procurement and ex vivo manipulation of such donor cells. Methods are disclosed for recruitment of a subject's own stem cells to a target region by inducing a sustained positive pressure at a target site, such as the kidney, thereby increasing the number of pluripotent cells capable of differentiating to regenerate the target tissue.

7 Claims, 17 Drawing Sheets

(56) References Cited

U.S. PATENT DOCUMENTS

| | | | |
|---|---|---|---|
| 2008/0260831 A1* | 10/2008 | Badylak | A61K 35/12 424/484 |
| 2009/0022777 A1* | 1/2009 | Mathiowitz | A61K 9/0024 424/425 |
| 2010/0094143 A1 | 4/2010 | Mahapatria et al. | |

OTHER PUBLICATIONS

Pourjavadi et al. "Salt- and pH-Resisting Collagen-based Highly Porous Hydrogel." Polymer Journal vol. 40, pp. 94-103 (2008) (Year: 2008).*
Miyanishi et al. "Do pluripotent stem cells exist in adult mice as very small embryonic stem cells?" Stem Cell Reports. Jul. 24, 2013;1(2):198-208. (Year: 2013).*
Dulak et al. "Adult stem cells: hopes and hypes of regenerative medicine." Acta Biochim Pol. 2015;62(3):329-37 (Year: 2015).*
Romito et al. "Pluripotent Stem Cells: Current Understanding and Future Directions." Stem Cells Int. 2016;2016:9451492. (Year: 2016).*
De Los Angeles et al "Hallmarks of pluripotency. . . " Nature. Sep. 24, 2015;525(7570):469-78 (Year: 2015).*
Asahara, T. et al. "Isolation of Putative Progenitor Endothelial Cells for Angiogenesis", Science, 275, pp. 964-967 (1997).
Atala, A. et al. "Tissue-Engineered Autologous Bladders for Patients Needing Cystoplasty", Lancet, 367, pp. 1241-1246 (2006).
Atala, A. "Recent Developments in Tissue Engineering and Regenerative Medicine", Curr Opin Pediatr, 18, pp. 167-217 (2006).
Athanasiou, Kyriacos A. et al. "Sterilization, Toxicity, Biocompatibility and Clinical Applications of Polylatic Acid/Polyglycolic Acid Copolymers", Biomaterials, vol. 17, No. 2, pp. 93-102 (1996).
Bartsch, G, et al. "Propagation, Expansion, and Multilineage Differentiation of Human Somatic Stem Cells From Dermal Progenitors", Stem Cells and Development, 14, pp. 337-348 (2005).
Chase et al., "Immobilization of Enzymes on Poly(vinyl alcohol)-Coated Perfluorocarbon Supports: Comparison of Tecniques for The Immobilization of Trypsin and x-amylase on Poly(vinyl alcohol)-Coated Solid and Liquid Perfluorocarbons", Biotechnol. Appl. Biochem, 27, pp. 205-216 (1998).
Cotran, Ramzi S. et al., "Pathologic Basis of Disease", Robbins—Sixth Addition, W.B. Saunders Company, (1999).
De Ugarte, Daniel A. et al. "Future of Fat As Raw Material for Tissue Regeneration", Annals of Plastic Surgery, vol. 50, No. 2, pp. 215-219 (Feb. 2003).
Deasy, Bridget M, Huard, Johnny, Gene Therapy and Tissue Engineering Based on Muscle-Derived Stem Cells, CurrentOpinion in Molecular Therapeutics, vol. 4, No. 4, pp. 382-389 (2002).
El-Kassaby, Abdel W., et al. "Urethral Stricture Repair With an Off-The-Shelf Collagen Matrix", The Journal of Urology, vol. 169, pp. 170-173 (2003).
Gage, Fred H. "Mammalian Neural Stem Cells", Science 287, pp. 1433-1438 (2000).
Guillot, Pascale V., et al. "Stem Cell Differentiation and Expansion for Clinical Applications of Tissue Engieering", J. Cell Mol. Med., vol. 11, No. 5, pp. 935-944 (2007).
Heumanson, Greg T., "Biconjugate Techniques", Academic Press San Diego, CA 1996.
Hu, Wen-Jing et al."Molecular Basis of Biomaterial-Mediated Foreign Body Reactions", Blood, 98, pp. 1231-1238 (2001).
Kimura, Keiichi et al. "Synthesis of Poly(vinyl Alcohol)-Based Poly(crown Ether)s and Permeability of Their Polymeric Membranes", Journal of Polymer Science, vol. 21, pp. 2777-2785 (1983).
Kirker-Head, Carl A., "Recombinant Bone Morphogenetic Proteins: Novel Substances For Enhancing Bone Healing", Veterinary Surgery, vol. 24, pp. 408-419 (1995).
Langer, Robert and Vacanti, Joseph P., "Tissue Engineering", Sicence, vol. 260, pp. 920-926 (May 14, 1993).

Lim, Franklin and Sun, Anthony M. "Microencapsulated Islets As Bioartifical Endocrine Pancreas", Sicence, vol. 210, No. 4472, pp. 908-910, (Nov. 21, 1980).
Babensee, Julia E., et al. "Host Response to Tissue Engineered Devices", Advanced Drug Delivery Reviews, 33 pps. 111-139 (1998).
Morehead, John, M. and Holt, Richard G. "Soft-Tissue Response to Synthetic Biomaterials", Otolaryngologic Clinic of North America, vol. 27, No., pp. 195-201 (Feb. 1994).
Ossendorf, Christian, et al. "Treatment of Posttraumatic and Focal Osteoar4thritic Cartilage Defects of The Knee With Autologous Polymer-Based Three-Dimensional Chondrocyte Grafts: 2-Year Clinical Results", Arthritis Research, 9/2/R41, pp. 1-11 (2007).
Overberger, C.G. and Chang, Ji Young "Synthesis of Optically Active Polynucleotide Analogs With Poly(vinyl Alcohol) is as Backbones and Adenine and 5-Bromouracil Derivatives As Pendants", Journal of Polymer Science, vol. 27, pp. 3589-3602 (1989).
Pfister, Otmar et al., "CD31-But Not CD31+ Cardiac Side Population Cells Exhibit Functional Cardiomyogenic Differentiation", Circulation Research—Journal of the American Heart Association, 97, pp. 52-61 (2005).
Shin'oka, Toshiharu et al., "Midterm Clinical Result of Tissue-Engineered Vascular Autografts Seeded With Autologous Bone Marrow Cells", The Journal of Thoracic and Cardiovascular Surgery, vol. 129, No. 6, pp. 1330-1338 (Jun. 2005).
Tang, Liping et al. "Molecular Determinants of Acute Inflammatory Responses to Biomaterials", J. Clin. Invest., vol. 97, N. 5, pp. 1329-1334 (Mar. 1996).
Tang, Liping et al. "Inflammatory Responses to Biomaterials", Basic Science, Am J.Clin Pathol, vol. 103, No. 4, pp. 466-471 (1995).
Williams, D.J. and Sebastine, I.M., "Tissue Engineering and Regenerative Medicine: Manufacturing Challenges", IEE Proc-Nanobiotechnol, vol. 152, No. 6, pp. 207-210 (Dec. 2005).
Wolters, Gerrit H.J. et al. "A Versatile Alginate Droplet Generator Applicable For Microencapsulation of Pancreatic Islets", Journal of Applied Biomerials, vol. 3, pp. 281-286 (1992).
Zhang, Ying et al. "Hepatic Stem Cells: Existence and Origin", World J. Gastroenterol, vol. 9, pp. 201-204 (2003).
Ciulla, Michele M. et al. "Effects of Simulated Altitude (normobaric hypoxia) on Cardiorespiratory Parameters and Circulating Endothelial Precursors in Healthy Subjects", Respir Res. vol. 8, No. 1:58, pp. 1-8 (2007).
Imasawa, Toshiyuki et al. "The Potential of Bone Marrow-Derived Cells To Differentiate to Glomerular Mesangial Cells", J. AM Soc Nephrol, vol. 12, No. 7, pp. 1401-1409 (Jul. 2001).
Miyanishi, Keita et al. Doese- and Time-Dependent Effects of Cyclic Hydrostatic Pressure on Transforming Growth Factor-$\ominus$-Induced Chondrogenesis by Adult Human Mesenchymal Stem Cells in Vitro.
Wallace, Donald G. and Rosenblatt, Joel "Collagen Gel Systems for Sustained Delivery and Tissue Engineering", Advance Drug Delivery Reviews, 55, pp. 1631-1649 (2003).
Slotkin, T.A. et al. "Fetal Dexamethasone Exposure Accelerates Development of Renal Function: Relationship to Dose, Cell Differentiation and Growth Inhibition", J. Dev Physiol, 17, pp. 55-61 (1992).
Hochman Mark et al., "Interstitial Tissue Pressure Associated With Dental Injections: A Clinical Study", Quintessence International, 37, pp. 469-476 (2006).
Collins English Dictionary—Complete & Unabridged 10th Edition [online], 2009 [retrieved on Jun. 14, 2012]. Retrieved from Dictionary.com Website:<URL: http://disctionary.reference.com/browse/hyperbaric>, definition of "Hyperbaric" under "World English Dictionary" section.
Unit Converter—Pressure Converter [online] [retrieved on Jun. 14, 2012]. Retrieved from Unit Converter website: <URL:http://www.unitconverters.net/pressure-converter.html>, "psi to centimeter water" conversion.

* cited by examiner

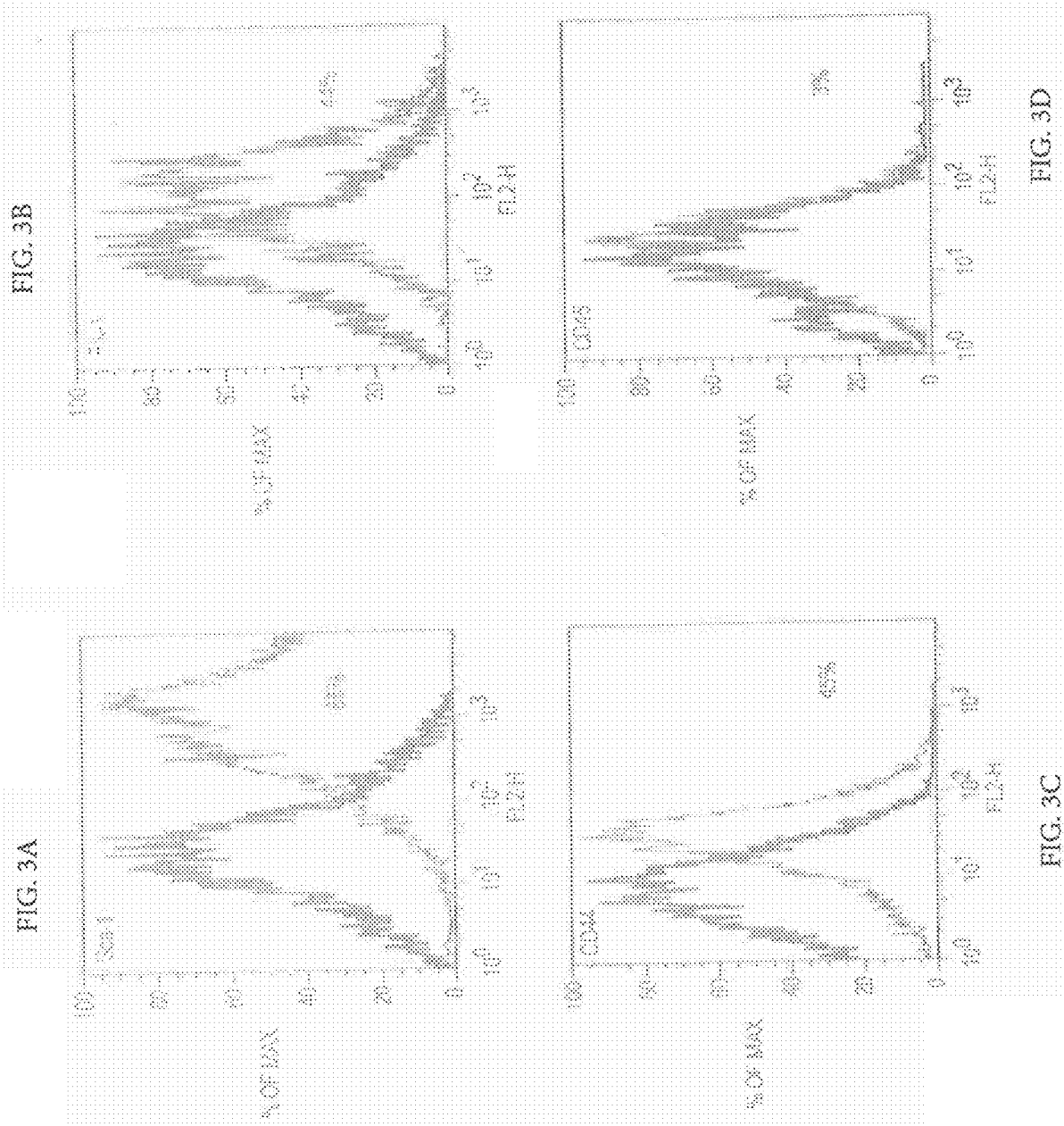

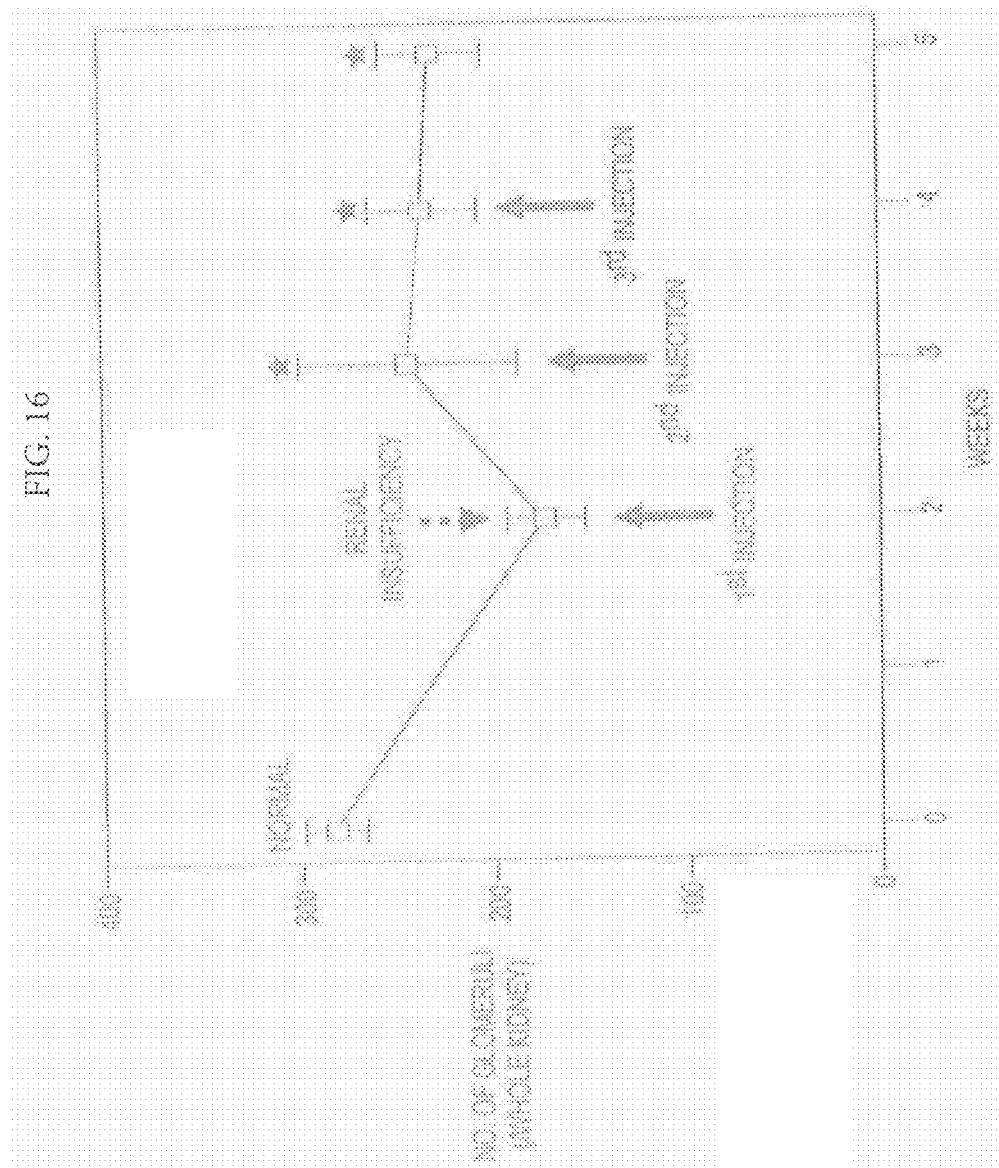

DIRECTED STEM CELL RECRUITMENT

CROSS-REFERENCE TO RELATED APPLICATIONS

The present application is a continuation of U.S. patent application Ser. No. 12/991,811, filed Jan. 10, 2011, which is a U.S. National 371 of PCT/US2009/43446, filed May 11, 2009, which claims benefit to Provisional Application No. 61/051,939, filed May 9, 208, the contents of which are hereby incorporated by reference in their entirety.

FIELD OF THE INVENTION

The present invention concerns tissue engineering and, in particular, methods of recruiting stem cells to a target site.

BACKGROUND OF THE INVENTION

Chronic renal disease is a common condition that elevates the risk of complete renal failure, cardiovascular disease and other complications. The prevalence of chronic renal failure has continuously increased in the United States in the last decade. Currently, the only treatment options for renal failure are dialysis and transplantation, both of which are associated with considerable cost. Dialysis, usually performed 3 times per week, impairs the patient's quality of life and does not replace renal functions such as synthesis of erythropoietin and vitamin D. Transplantation, on the other hand, can replace all renal functions, but the rising occurrence of end stage renal disease (ESRD) in the United States continues to outpace the rate of organ donation, as reflected by the fact that the waiting list continues to grow by 3,000 to 4,000 people per year. Furthermore, long-term results of kidney transplantation remain unsatisfactory, mainly because of chronic rejection and complications associated with immunosuppressive medications. Therefore, novel therapies for renal failure are needed.

A major goal of tissue engineering and reconstructive surgery is the restoration of structure and function to damaged organs or tissue. While the body's normal reparative processes can heal small, localized injuries, a large traumatic injury will often overwhelm the body's natural restorative systems and result in a deficit of functional recovery, despite the use of conventional reconstructive modalities. Organ transplantation has become increasingly commonplace in life-threatening situations, Such transplantations involve moving a whole or partial donor organ to replace a recipient's damaged or failing one.

However, problems exist when biological material is transferred from one individual to another. Organ rejection is a significant risk associated with transplantation, even with a good histocompatibility match. Immunosuppressive drugs such as cyclosporin and FK506 are usually given to the patient to prevent rejection. These immunosuppressive drugs however, have a narrow therapeutic window between adequate immunosuppression and toxicity. Prolonged immunosuppression can weaken the immune system, which can lead to a threat of infection. In some instances, even immunosuppression is not enough to prevent organ rejection. Another major problem of transplantation is the availability of donor organs. In the United States alone there are about 100,000 people on transplant waiting lists, many of whom will die before an organ becomes available.

Cell-based approaches using tissue engineering and regenerative medicine techniques have offered new therapeutic opportunities for various pathologic conditions. During the past decade, a number of different approaches for engineering renal tissue have been attempted. The goal of each approach was to replace or recover some renal functions. These require several important methodological choices and a number of technical difficulties have been encountered. Although the fundamental principles of cell-based therapies have been demonstrated on multiple tissue systems clinically, it usually necessitates a donor tissue biopsy and ex vivo cell manipulation prior to implantation in vivo. One of the most critical initial steps is the choice of an appropriate cell source. For typical tissue engineering approaches, cells need to be expanded in large quantities, while maintaining uniform activity and remaining pathogen-free. Moreover, the kidney is an extremely complex structure which consists of at least 26 terminally differentiated cell types, including tubular epithelial cells, interstitial cells, glomerular cells and vascular cells.

Most recently, stem cells have been identified as an alternative source of cells for tissue regeneration. However, current protocols for the use of stem cells for regeneration typically require harvesting tissues for cell retrieval, isolation of stem cells, in vitro expansion and/or differentiation of the isolated stem cells, and reimplantation of the manipulated cells into specific tissue sites in vivo for restoration of organ/tissue function.

There exists a need for better methods of tissue regeneration. In particular, new methods of restoring structure and/or function to damaged or failing body structures would satisfy a long-felt therapeutic need.

SUMMARY OF THE INVENTION

The invention is based, in part, on the discovery that a subject's own biologic resources and environmental conditions can be used for in situ tissue regeneration and thereby reduce or eliminate the need for donor cell procurement and ex vivo manipulation of such donor cells. Methods and compositions are disclosed for recruitment of a subject's own stem cells to a target region by inducing a sustained positive pressure at a target site.

This invention reduces or eliminates the need for laborious stem cell isolation and ex vivo cell culturing by directly recruiting a stem cell population into target specific sites for regeneration in vivo. This is possible due to the nature of host cellular responses to environment changes. In one aspect of the invention, the use of a biocompatible substance as an implant can be used to recruit pluripotent cells to a target site within a body structure and induce tissue regeneration within the body structure in vivo using a "directed cell recruitment" technique. Moreover, a method can be directed to inducing cell recruitment to a target site by delivering a biocompatible substance to a target site within a body structure to produce positive pressure within the target site and maintaining the positive pressure, such that pluripotent cells are recruited to the target site. Another aspect can be directed to a method of inducing in situ tissue regeneration at a target site of a subject by delivering a biocompatible substance to the target site to produce a positive pressure, maintaining the positive pressure for a period of time such that the number of pluripotent cells is increased at the target site, delivering at least one adjuvant to the target site and promoting differentiation of the pluripotent cells to regenerate the tissue.

To demonstrate this technique, several injectable scaffolds have been used to show that cell recruitment assisted regeneration is possible in a rodent kidney model. Kidney structures, including glomeruli and tubules, were formed within the injected gel scaffolds in the renal parenchyma 1 week after injection and continued to mature with time.

Current treatment options for renal failure are extremely limited and only renal transplantation can restore kidney function. This invention can provide an alternative treatment modality for patients with renal failure. The outcome of kidney tissue regeneration suggests that this technology can be applied in other organ/tissue systems. One aspect of the invention can be directed to kidney regeneration by injecting a substantially cell-free biocompatible substance into a target site in a kidney, such that the biocompatible substance creates a hyperbaric environment at the target site, maintaining the positive pressure for at least one hour to recruit pluripotent cells, and inducing differentiation of the pluripotent cells to produce new glomeruli structures.

As shown in the examples, collagen based gel scaffolds, and other biomaterials, including collagen type I, collagen based kidney tissue gel matrix, synthetic gel matrix and keratin based gel matrix were tested in regeneration of kidney tissues. The results of all injections demonstrated similar findings with formation of glomerular and tubular structures. Thus, stem cells or progenitor cells can be recruited to target specific sites, and corresponding cells and tissues can be formed.

The recruited stem cells can be differentiated into target tissues for regeneration. Various tissues and organ systems can be regenerated using the methods of the present invention, including, but not limited to, kidney, liver, spleen, pancreas, muscle, heart, skin, lung, cartilage, spinal cord, bone, spleen, bladder, ureter, urethra, intestine, thymus, and thyroid.

In another aspect, the invention discloses a method inducing cell recruitment to a target site of a subject, preventing inflammatory cells, and/or reducing collagen deposition at and around the site. The biocompatible substance can also comprise at least one adjuvant delivered to the target site, and/or incorporated into the biocompatible substance. The adjuvant can be incorporated in or on the biocompatible substance and can be delivered separate from the biocompatible substance. The adjuvant can be selected from growth factors, cytokines, enzymes, collagen reducing agents, antibiotics and anti-inflammatory agents. The adjuvants can also be, for example, anti-inflammatory agents and/or collagen synthetase inhibitors. In preferred embodiments, the anti-inflammatory agents counteract or suppress the inflammatory process. In some embodiments, the anti-inflammatory agent is a collagen synthetase inhibitor. Anti-inflammatory agents can be steroidal or non-steroidal. Non-limiting examples of anti-inflammatory agents include, corticosteroids, dexamethasone, rapamycin, paclitaxel, ABT-578, everolimus, taxol, steroidal anti-inflammatory agents, non-steroidal anti-inflammatory agents, hemostatic agents; antimicrobial agents; antibiotics; antifungals; antiprotozoals; antivirals; antimicrobial metals; hemostatic and/or vasoconstricting agents; pseudoephedrine; xylometazoline; oxymetazoline; phenylephrine; epinephrine; cocaine; local anesthetic agents; lidocaine; cocaine; bupivacaine; hormones; hormonally active agents; agents that enhance potency; substances that dissolve, degrade, cut, break, weaken, soften, modify or remodel connective tissue or other tissue; enzymes; trypsin; EDTA; trypsin combined with EDTA; hyaluronidase; tosyllysylchloromethane (TLCM); chemotherapeutic or antineoplastic agents; substances that prevent adhesion formation; hyaluronic acid gel. Non-limiting examples of collagen synthetase inhibitors include collagenase, halofuginone, propyl hydroxylase, c-proteinase inhibitor, and metalloproteinase. In a preferred embodiment, the adjuvant can be collagen synthetase inhibitor, such as collagenase. In another preferred embodiment, the adjuvant can be an anti-inflammatory agent, such as dexamethasone.

The examples were performed in the subcutaneous tissue system in order to show that stem cells can be directed into specific target sites. This system can be applied in other tissues or organ systems. Synthetic materials were used to demonstrate that no biological factors were needed to recruit stem cells to the target site. In some embodiments of the invention, biological scaffolds incorporating cell and/or tissue differentiation factors can be combined to regenerate tissues in vivo. The biocompatible substance can be a natural or synthetic polymer. The biocompatible substance can take any form, such as implantable or injectable biomaterials, such as a hydrogel. In one embodiment, the biocompatible substance is a substantially cell-free, injectable biocompatible polymeric substance. Preferable, the biocompatible substance is sufficiently porous to allow cell infiltration. Also, the biocompatible substance can provide a scaffold for attachment of the pluripotent cells. In a preferred embodiment, the biocompatible substance can be a hydrogel formulated to expand by water absorption following implantation at the target site to provide a sustained positive pressure. In a preferred embodiment, the biocompatible substance is collagen. In another preferred embodiment, the biocompatible substance can comprise a solution having a collagen concentration from about 1 mg/ML to about 30 mg/ML. More preferably, the collagen solution thermogels at about 37° C.

In another aspect, the invention discloses target specific gel scaffolds. These target specific gel scaffolds can maximize the tissue regenerative capacity. Incorporation of factors, such as growth factors, extracellular matrix (ECM) proteins and bioactive molecules into the gel scaffold system can enhance tissue formation. This gel system can be used as a preventive measure in subjects with high risk of organ or tissue failure. The scaffolds can take various forms, depending on the tissue and its use. The biocompatible substance can be delivered into the target site via injection, surgically placing the substance into the target site, or by using a catheter.

In another aspect, the invention discloses tissue and/or organ specific scaffolds for regenerating, restoring, and/or augmenting various diseased tissues and organs. The tissue and/or organ specific scaffold can be used, for example, in subjects with or at risk for organ failure, or as preventive measures for organ maintenance.

In yet another aspect, the invention provides a method of inducing cell recruitment to a target site of a subject comprising delivering a biocompatible substance into a target site capable of producing a sustained increase in positive pressure within the target site, and maintaining the increase in positive pressure at the target site for a period of time, whereby the number of pluripotent cells at the target site is increased. The positive pressure is capable of being sustained between about 5 cmH$_2$O to about 70 cmH$_2$O, or about 5 cmH$_2$O to about 50 cmH$_2$O, or about 10 cmH$_2$O to about 40 cmH$_2$O, or about 10 cmH$_2$O to about 30 cmH$_2$O, or about 15 cmH$_2$O to about 35 cmH$_2$O, or about 20 cmH$_2$O to about 30 cmH$_2$O after delivery at the target site. In some embodiments, the biocompatible substance has a viscosity between about 5 cP to about $1\times10^8$ cP, or about 5 cP to about $1\times10^6$ cP, or about 5 cP to about $1\times10^5$ cP, or about 5 cP to about $1\times10^4$ cP, or about 10 cP to about $1\times10^3$ cP, or about 6 cP to about 9500 cP at 25° C.

DESCRIPTION OF THE DRAWINGS

FIG. 1 shows histological evaluations of the implanted cell-free scaffolds.

FIGS. 3A-3H are FACS analysis graphs of infiltrating cells characterized for expression of various markers. FIG. 3A is a FACS graph for expression of Sca-1; FIG. 3B is a FACS graph for expression of Flk-1; FIG. 3C is a FACS graph for expression of CD44 (C); FIG. 3D is a FACS graph for expression of CD45; 3E is a FACS graph for expression of CD31; FIG. 3F is a FACS graph for expression of CD34, FIG. 3G is a FACS graph for expression of CD90, and FIG. 3H is a FACS graph for expression of CD117. Isotype-matching IgG and a FITC-labeled secondary antibody were used to determine nonspecific signals.

FIG. 12A shows the number of glomeruli per whole kidney area and FIG. 12B shows the number of glomeruli per mm2 (*$P<0.05$).

FIG. 14A shows partial pressure measurements in a mouse kidney and FIG. 14B shows partial pressure measurements in a rat kidney.

FIG. 16 shows multiple injections with different time points. Number of glomeruli of the whole kidney after collagen gel injection with multiple time points ($P<0.05$).

DETAILED DESCRIPTION

Figures 1A, 1B:
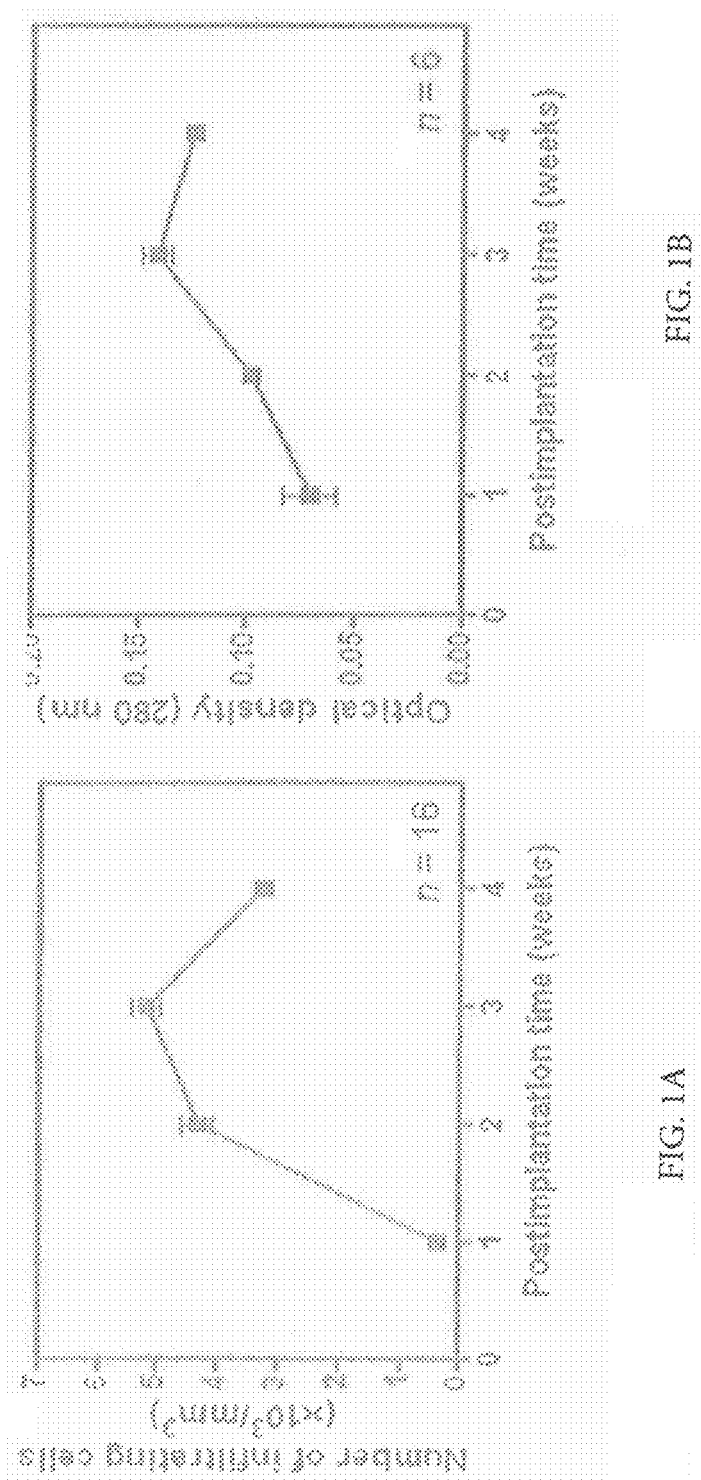
FIG. 1A shows the number of recruiting cells. The infiltrating cells gradually increased in number up to 3 weeks after implantation.
FIG. 1B shows DNA content in the implanted scaffold. DNA content indicates cellularity within the implanted scaffold. DNA content gradually increased up to 3 weeks after implantation.

The invention is directed to methods of inducing cell recruitment and tissue regeneration at a target site in a subject. It is also based, in part, on the discovery that a subject's own biologic resources and environmental conditions can be used for in situ tissue regeneration and thereby reduce or eliminate the need for donor cell procurement and ex vivo manipulation of such donor cells. Methods are disclosed for recruitment of a subject's own stem cells to a target region by inducing a sustained positive pressure at a target site, such as the kidney, thereby increasing the number of pluripotent cells capable of differentiating to regenerate the target tissue.

As shown in the examples, a common biomaterial was implanted into mice and the infiltrating cells were characterized to determine their regenerative potential. In contrast to prior belief, the host cell infiltrates are not entirely comprised of inflammatory and fibroblast-like cells. The normal inflammatory process can be altered by incorporating anti-inflammatory agents that influence the formation of scar tissue. In addition, the infiltrating cells are capable of differentiating into multiple cell lineages, including osteogenic, myogenic, adipogenic and endothelial, if appropriate conditions are provided. The examples show that it is possible to recruit a predominance of cells with multilineage potential into a biomaterial scaffold. The infiltrate can be enriched with such cell types and their fate can be controlled, provided the proper substrate-mediated signaling is imparted into the scaffold for in situ tissue regeneration.

A typical clinical solution for repairing large tissue defects is to restore some level of function through the use of an implant. Surgical implants can consist of autografts (e.g. tissue flaps), allografts (e.g. cadaveric tissues), and a multitude of synthetic and naturally derived biomaterials. Although many of these modalities are able to achieve the targeted goals, various limitations remain a challenge, which ranges from donor tissue unavailability to procedure related complications. Recent advances in tissue engineering and regenerative medicine have offered new opportunities for treatment of tissue and organ deficits. Various cell and biomaterial related technologies have allowed for the development of biological substitutes which are designed to restore and maintain normal tissue and organ function (Atala A. Recent developments in tissue engineering and regenerative medicine. *Curr Opin Pediatr* 2006; 18:167-171; Williams D J, Sebastine I M. Tissue engineering and regenerative medicine: manufacturing challenges. *IEE Proc Nanobiotechnol* 2005; 152:207-210).

Classic tissue engineering approaches have been employed to overcome the present challenges by implementing biomaterial scaffolds that are pre-seeded with desirable cell types to generate functional tissues that progressively mature when introduced in vivo. Using this strategy, many pathologic tissue conditions such as urethral stricture, bladder dysfunction, vascular grafts, and osteoarthritic cartilage defect, have been treated clinically. (El-Kassaby A W, Retik A B, Yoo J J, Atala A. Urethral stricture repair with an off-the-shelf collagen matrix. *J Urol* 2003; 169:170-173; Atala A, Bauer S B, Soker S, Yoo J J, Retik A B. Tissue-engineered autologous bladders for patients needing cystoplasty. *Lancet* 2006; 367:1241-1246; Shin'oka T, Matsumura G, Hibino N, Naito Y, Watanabe M, Konuma T, Sakamoto T, Nagatsu M, Kurosawa H. Midterm clinical result of tissue-engineered vascular autografts seeded with autologous bone marrow cells. *J Thorac Cardiovasc Surg* 2005; 129:1330-1338; Ossendorf C, Kaps C, Kreuz P C, Burmester G R, Sittinger M, Erggelet C. Treatment of posttraumatic and focal osteoarthritic cartilage defects of the knee with autologous polymer-based three-dimensional chondrocyte grafts: 2-year clinical results. *Arthritis Res Ther* 2007; 9:R41.). Although the principle of this technology has been demonstrated in various preclinical and clinical studies in different tissue systems, the approach has typically necessitated a donor tissue biopsy, followed by cell isolation and expansion which requires extensive cell manipulation prior to implantation in vivo. (Langer R, Vacanti J P. Tissue engineering. *Science* 1993; 260:920-926.) In instances where donor cells are unavailable due to extensive tissue damage, stem and progenitor cells have been considered as alternate cell sources. However, the use of these cells requires a similar approach including ex vivo procedures such as expansion and/or differentiation into specific cell lineages for cell-based therapies. (Guillot P V, Cui W, Fisk N M, Polak D J. Stem cell differentiation and expansion for clinical applications of tissue engineering. *J Cell Mol Med* 2007; 1 1:935-944.)

Simplifying these processes by eliminating a tissue biopsy and in vitro cell isolation, expansion and differentiation steps would provide a more efficient means of developing biological substitutes for functional tissue restoration in vivo. This proposition may be possible by tapping the body's innate regenerative systems which have all the biological resources necessary for tissue regeneration. It is widely accepted that almost every tissue in the body contains some type of stem or progenitor cells, including brain, liver, circulating blood, heart, skin, fat and muscle. (Gage F H. Mammalian neural stem cells. *Science* 2000; 287:1433-1438; Zhang Y, Bai X F, Huang C X. Hepatic stem cells: existence and origin. *World J Gastroenterol* 2003; 9:201-204; Asahara T, Murohara T, Sullivan A, Silver M, van der Z R, Li T, Witzenbichler B, Schatteman G, Isner J M. Isolation of putative progenitor endothelial cells for angiogenesis. *Science* 1997; 275:964-967; Pfister O, Mouquet F, Jain M, Summer R, Helmes M, Fine A, Colucci W S, Liao R. CD31– but not CD31+ cardiac side population cells exhibit functional cardiomyogenic differentiation. *Circ Res* 2005; 97:52-61; Bartsch G, Yoo J J, De C P, Siddiqui M M, Schuch G, Pohl H G, Fuhr J, Perin L, Soker S, Atala A. Propagation, expansion, and multilineage differentiation of human somatic stem cells from dermal progenitors. *Stem Cells Dev* 2005; 14:337-348; De Ugarte D A, Ashjian P H, Elbarbary A, Hedrick M H. Future of fat as raw material for tissue regeneration. *Ann Plast Surg* 2003; 50:215-219; Deasy B M, Huard J. Gene therapy and tissue engineering based on muscle-derived stem cells. *Curr Opin Mol Ther* 2002; 4:382-389.) It would seem that these cells are part of underlying regenerative machinery that is responsible for daily maintenance activities, including repair of normal tissue wear and tear, as well as small, non-life threatening types of injuries. However, when extensive tissue damage occurs and large tissue defects are present, the regenerative response is overwhelmed and an immune-based reparative response takes over to maintain some level of function. (Cotran R Z, Kumar V, Robbins S L. Robbins Pathologic Basis of Disease. Philadelphia, Pa., W B Saunders, 1999) While the immediate problem may be mitigated by these reparative processes, responses such as inflammation which results in uncontrolled collagen deposition and fibrosis are undesirable because they can lead to further complications and severe deficits in tissue and organ functionality. (Morehead J M, Holt G R. Soft-tissue response to synthetic biomaterials. *Otolaryngol Clin North Am* 1994; 27:195-201; Tang L, Eaton J W. Inflammatory responses to biomaterials. *Am J Clin Pathol* 1995; 103:466-471; Tang L, Ugarova T P, Plow E F, Eaton J W. Molecular determinants of acute inflammatory responses to biomaterials. *J Clin Invest* 1996; 97:1329-1334; Mikos A G, McIntire L V, Anderson J M, Babensee J E. Host response to tissue engineered devices. *Adv Drug Deliv Rev* 1998; 33:111-139; Hu W J, Eaton J W, Ugarova T P, Tang L. Molecular basis of biomaterial-mediated foreign body reactions. *Blood* 2001; 98:1231-1238.)

Toward this goal, it can be established that the host cell infiltrate that accompanies every foreign body reaction has at least some capacity for regeneration. However, this notion conflicts with the current dogma that the host cell infiltrate is comprised primarily of immune and fibroblast-like cells, which are believed to be responsible for the formation of scar tissue. Remarkably, this conclusion has been reached in the absence of definitive experiments that incorporate the use of unique, specific immunohistochemical markers capable of identifying the cell types in retrieved biomaterial implants. A first step in reversing this historical tenet is to demonstrate the host cell infiltrate contains cells other than fibroblast-like cells. As shown in the examples, an animal model was used to initiate cell infiltration into an implanted biomaterial, followed by extensive and definitive characterization of that cell infiltrate. The examples demonstrate the use of infiltrating host cells as an in situ source for tissue regeneration, which can be used for donor cell procurement and subsequent in vitro cell manipulation.

A normal human body possesses biologic resources and an ideal environment for recovery from tissue damage due to various insults. This is usually achieved through normal wound healing process which is initiated by inflammatory and immunologic responses. While small and minor wounds can be repaired through this process without causing functional tissue abnormalities, large tissue defects due to extensive tissue trauma usually results in a functional deficit. In such instances, various reconstructive measures are necessary to restore functionality of the affected tissues and organs. Cell based approaches using tissue engineering and regenerative medicine techniques have been employed to repair defects for partial or full restoration of affected tissue function. However-, these approaches usually require cell/tissue biopsy and extensive cell manipulation in vitro prior to implantation in vivo.

Functional recovery in acute renal failure has been demonstrated recently. Several researchers have reported the existence of renal stem/progenitor cells which can contribute to regeneration and repair in the kidney. Several genes expressed during embryonic development are downregulated in mature kidney tissue, but are expressed again during recovery after renal injury. One such factor is paired box gene 2 (PAX-2). PAX-2 belongs to a family of transcription factors, and is required for development and proliferation of renal tubules. Renal progenitor cells expressing CD24, CD133, and PAX-2 have been identified at the tubular and glomerular levels and can regenerate tubular cells in an animal model of acute renal failure. It has been demonstrated that the presence of a resident population of stem cells expressing CD 133 and PAX-2 markers in adult normal human kidney are capable of expansion and, potentially, self-renewal. In addition, bone marrow-derived cells represent potential source of cells that can regenerate renal tubules. The presence of an underlying regenerative mechanism in the form of tissue specific stem and progenitor cells suggests that there can be an opportunity to bias the host response toward repair of renal injury.

The invention discloses methods of utilizing the body's biologic and environmental resources in situ for tissue regeneration. The examples demonstrate whether implantation of cell-free biomaterials can recruit host cells that can participate in the tissue repairing process. A large proportion of infiltrated host cells within the biomaterial implants was demonstrated to have multilineage potential (i.e. 85% by flow cytometry analysis). Using standard protocols for immunocytochemistry and flow cytometry, we confirmed that these cells are able to express a hematopoietic stem cell marker, Sca-1. However, these cells did not express endothelial progenitor markers such as Flk-1, CD31, CD34, or CD45; nor did they express mesenchymal stem cell markers, including CD44, CD45, CD90, or CD117. Sca-1 expression persisted for over five consecutive subcultures. Moreover, differentiation experiments demonstrated that these cells are able to transform into osteogenic, endothelial, adipogenic, and myogenic lineages. These results indicate that many of the cells that are mobilized into a biomaterial are multipotent, and given an optimal environment, they can differentiate into specific cell types functional for regenerating the implant site.

To examine the effects of environmental cues on the infiltrating cells and to determine whether normal host response can be altered, dexamethasone, a well-known anti-inflammatory corticosteroid, was incorporated into the biomaterial implants. This environment allowed host cell infiltration but delayed collagen deposition within the target sites over time (FIG. 5). This finding demonstrates that removal of pro-inflammatory signals can allow the multipotent cells present in the scaffold to initiate a regenerative process. This experiment indicates that environmental cues can be controlled and further suggests that host cells can be utilized and manipulated in situ for target tissue regeneration.

I. Definitions

So that the invention may more readily be understood, definitions known by those skilled in the art are described below:

The phrases "augmenting organ function" or "augmenting function of an organ" as used herein refers to increasing, enhancing or improving the function of an organ or body structure that is operating at less than optimum capacity. The term is used to refer to a gain in function so that the organ or structure is operating at a physiologically acceptable capacity for that subject. For example, the physiological acceptable capacity for an organ from a child, e.g., a kidney or heart, would be different from the physiological acceptable capacity of an adult, or an elderly patient. The entire organ or part of the organ can be augmented. Preferably the augmentation results in an organ with the same physiological response as a native organ. In a preferred embodiment, an organ is augmented in capacity when it is functioning to at least at 10% of its natural capacity.

The phrase "biocompatible substance" and term "biomaterial" are used interchangeably and refer to a material that is suitable for implantation or injection into a subject. A biocompatible substance does not cause toxic or injurious effects once implanted in the subject. In one embodiment, the biocompatible substrate is a polymer with a surface that can be shaped into the desired structure that requires repairing or replacing. The polymer can also be shaped into a part of a body structure that requires repairing or replacing. In another embodiment, the biocompatible substrate can be injected into a subject at a target site.

As used herein, the term "stem cell" refers to a master cell that can reproduce indefinitely to form the specialized cells of tissues and organs. The terms "stem cell" and "pluripotent cell" are used interchangeably herein. A stem cell (or pluripotent) can divide to produce two daughter stem cells, or one daughter stem cell and one progenitor ("transit") cell, which then proliferates into the tissue's mature, fully formed cells. The "stem cell" used herein includes "progenitor cells" unless otherwise noted. The term "pluripotential", "pluripotential for differentiation" or "pluripotent" can also refer to a cell that is positive for one or more of the pluripotent markers such as but are not limited to Oct-4, Nanog, and Sox-2 and the cell has the potential to differentiate to at least a subset of the mammalian body's approximately 260 cell types upon appropriate stimulations such as by the appropriate growth factors.

The term "subject," as used herein, refers to any living organism capable of eliciting an immune response. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or gender. Thus, adult and newborn subjects, as well as fetuses, whether male or female, are intended to be covered.

The term "target site" as used herein refers to region in the organ or body structure that requires augmentation. The target site can be a single region in the organ, or can be multiple regions in the organ. The entire organ or part of the organ can be augmented. Preferably the augmentation results in an organ with the same physiological response as a normal organ. The entire organ can be augmented by placing a plurality of biomatrices at suitable distances along the entire organ, e.g., along the entire longitudinal section of a kidney. Alternatively, part of the organ can be augmented by placing at least one biomatrix in one target site of the organ, e.g., the top of the kidney.

II. Biomaterials

The phrase "biocompatible substance" and term "biomaterial" are used interchangeably and refer to a material that is suitable for implantation or injection into a subject. A biocompatible substance does not cause toxic or injurious effects once implanted in the subject. In one embodiment, the biocompatible substrate is a polymer with a surface that can be shaped into the desired structure that requires repairing or replacing. The polymer can also be shaped into a part of a structure that requires repairing or replacing. In another embodiment, the biocompatible substrate can be injected into a subject at a target site. Preferably, the biocompatible substance can be an attachment structure for cells promoting cell recruitment and tissue regeneration.

Preferably, the biocompatible substance can create a hyperbaric environment at the target site. The biocompatible substance can also provide sustained positive pressure between about 5 cmH$_2$O to about 70 cmH$_2$O, or about 5 cmH$_2$O to about 50 cmH$_2$O, or about 10 cmH$_2$O to about 40 cmH$_2$O, or about 10 cmH$_2$O to about 30 cmH$_2$O, or about 15 cmH$_2$O to about 35 cmH$_2$O, or about 20 cmH$_2$O to about 30 cmH$_2$O, for a period of time, and has a viscosity greater than that of water. For example, the biocompatible substance is capable of providing sustained positive pressure for longer than about 1 hour, longer than about 12 hours, longer than about 1 day, longer than about 3 days, longer than about 5 days, longer than about 10 days, longer than about two weeks. The examples demonstrate that created space is insufficient for tissue regeneration indicating that pressure can influence cell recruitment, preferably stem cell recruitment, of native cells in the tissue into the target area to initiate the regenerative process. In some embodiments, the biocompatible substance has a viscosity between about 5 cP to about 1×10$^8$ cP, or about 5 cP to about 1×10$^6$ cP, or about 5 cP to about 1×10$^5$ cP, or about 5 cP to about 1×10$^4$ cP, or about 10 cP to about 1×10$^3$ cP, or about 6 cP to about 9500 cP at 25° C.

Natural or synthetic polymers can be used as the biocompatible substance. Synthetic polymers that can be used to form the microspheres include bioerodible polymers such as poly(lactide) (PLA), poly(glycolic acid) (PGA), poly(lactide-co-glycolide) (PLGA), poly(caprolactone), polycarbonates, polyamides, polyanhydrides, polyamino acids, poly-ortho esters, polyacetals, polycyanoacrylates and degradable polyurethanes, and non-erodible polymers such as polyacrylates, ethylene-vinyl acetate polymers and other acyl substituted cellulose acetates and derivatives thereof, non-erodible polyurethanes, polystyrenes, polyvinyl chloride, polyvinyl fluoride, poly(vinylimidazole), chlorosulphonated polyolefins, and polyethylene oxide. Examples of natural polymers include proteins such as collagen, albumin, synthetic polyamino acids, and prolamines, and polysaccharides such as alginate, heparin, and other naturally occurring biodegradable polymers of sugar units.

In some embodiments, the biocompatible substance can have incorporated biomaterials, such as polymers used to encapsulate growth factors, drugs, or other agents which can be released at the target site. The normally charged outer layer of the microcapsules can be covered by water soluble non-ionic polymers such as poly(ethylene oxide) (PEO) which act to shield the charge. These polymers are grafted to the polycationic polymers, such as poly-L-lysine (PLL) molecules used as at least one of the layers of the microcapsule, such that they create a non-ionic barrier between the outer layer of the microcapsule (made of essentially either polycationic polymers, such as PLL, or polyanionic polymers, such as alginate) and the target tissue.

PLA, PGA and PLA/PGA copolymers are particularly useful for forming microspheres. PLA polymers are usually prepared from the cyclic esters of lactic acids. Both L(+) and D(−) forms of lactic acid can be used to prepare the PLA polymers, as well as the optically inactive DL-lactic acid mixture of D(−) and L(+) lactic acids. Methods of preparing polylactides are well documented in the patent literature. The following U.S. Patents, the teachings of which are hereby incorporated by reference, describe in detail suitable polylactides, their properties and their preparation: U.S. Pat. No. 1,995,970 to Dorough; U.S. Pat. No. 2,703,316 to Schneider; U.S. Pat. No. 2,758,987 to Salzberg; U.S. Pat. No. 2,951,828 to Zeile; U.S. Pat. No. 2,676,945 to Higgins; and U.S. Pat. Nos. 2,683,136; 3,531,561 to Trehu.

By altering the properties of the polymer and the properties of the dosage form, one can control the contribution of each of these release mechanisms and alter the release rate of factors. Slowly eroding polymers such as poly(L-lactide) or high molecular weight poly(lactide-co-glycolide) with low glycolide compositions will cause the release to become diffusion controlled. Increasing the glycolide composition and decreasing the molecular weight enhances both water uptake and the hydrolysis of the polymer and adds an erosion component to the release kinetics. In a preferred embodiment, the biocompatible substance comprises alginate-PLL capsules.

A biocompatible substance can also be biodegradable. Biodegradable refers to material that can be absorbed or degraded in a patient's body. Representative materials for forming the biodegradable structure include natural or synthetic polymers, such as, for example, collagen, poly (alpha esters) such as poly (lactate acid), poly (glycolic acid) (PGA), polyorthoesters and polyanhydrides and their copolymers, which degraded by hydrolysis at a controlled rate and are reabsorbed. These materials provide the maximum control of degradability, manageability, size and configuration. Preferred biodegradable polymer materials include polyglycolic acid and polygalactin, developed as absorbable synthetic suture material. Polyglycolic acid and polygalactin fibers may be used as supplied by the manufacturer. Other biodegradable materials include cellulose ether, cellulose, cellulosic ester, fluorinated polyethylene, phenolic polymer, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, poly vinyl, polyvinylidene fluoride, regenerated cellulose, silicone, urea-formaldehyde, or copolymers or physical blends of these materials. The material can be impregnated with suitable antimicrobial agents and can be colored by a color additive to improve visibility and to aid in surgical procedures.

The biocompatible substance can be non-biodegradable such that a growth factor or agent encapsulated in a biodegradable substance can be secreted through the biocompatible substance in a controlled release manner while the biocompatible substance remains. Semipermeable microcapsules can be produced through interfacial polymerization as described in U.S. Pat. No. 4,251,387. In a preferred embodiment, alginate-PLL capsules are used. Microencapsulation generally involves three steps: (a) generating microcapsules (e.g., by forming droplets of liquid alginate followed by exposure to a solution of calcium chloride to form a solid gel), (b) coating the resulting gelled spheres with additional outer coatings (e.g., outer coatings comprising polylysine and/or polyornithine) to form a semipermeable membrane; and (c) liquefying the original core gel (e.g., by chelation using a solution of sodium citrate). The three steps are typically separated by washings in normal saline.

Alginates are linear polymers of mannuronic and guluronic acid residues. Monovalent cation alginate salts, e.g., Na-alginate, are generally soluble. Divalent cations such as Ca$^{2+}$, Ba$^{2+}$ or Sr$^{2+}$ tend to interact with guluronate, providing crosslinking and forming stable alginate gels. Alginate encapsulation techniques typically take advantage of the gelling of alginate in the presence of divalent cation solutions. Alginate encapsulation generally involves encapsulation in a solution of a monovalent cation alginate salt to generate droplets of this solution, and contacting the droplets with a solution of divalent cations. The divalent cations interact with the alginate at the phase transition between the droplet and the divalent cation solution, resulting in the formation of a stable alginate gel matrix being formed. A variation of this technique is reported in U.S. Pat. No. 5,738,876, wherein the cell is suffused with a solution of multivalent ions (e.g., divalent cations) and then suspended in a solution of gelling polymer (e.g., alginate), to provide a coating of the polymer. In some embodiments, the biocompatible substance can be a hydrogel.

While it is well known that implants can become populated with host cells that can result in scar tissue, the cell types have previously been assumed to be inflammatory and fibroblastic, as indirect evidence (i.e. the presence of collagen) has suggested that fibroblasts are the predominant cell population present after the initial inflammation has subsided. As shown in the examples, a simple approach was used to address this dogma by using PGA nonwoven implants. This polymer has been widely used in tissue engineering and regenerative medicine as a biocompatible, biodegradable, and implantable biomaterial. PGA can be used as a synthetic biomaterial because the host immune response to PGA scaffolds has been well characterized by many investigators in a multitude of animal models, demonstrating that it induces a classic foreign body reaction. (Athanasiou K A, Niederauer G G, Agrawal C M. Sterilization, toxicity, biocompatibility and clinical applications of polylactic acid/polyglycolic acid copolymers. *Biomaterials* 1996; 17:93-102.). The PGA mesh used in this study is highly porous and is designed to increase diffusion and accommodate host cell infiltrates. Experimental results show that the number of host cells continue to increase up to 3 weeks after implantation and begin to decrease thereafter as collagen accumulates and fills the pores of PGA mesh. This is consistent with normal inflammatory response seen in many tissue systems.

This invention demonstrates that host cell infiltrates into a biomaterial implant are not entirely comprised of inflammatory and fibroblast-like cells. In the Examples it is shown that cells expressing hematopoietic markers are mobilized into the biomaterial and that these cells are capable of differentiating into multiple cell lineages if appropriate conditions are provided. In other aspect, the invention provides a tissue-specific cell-free biomaterial that can be universally applied to any patient, without the need for ex vivo cell manipulation. Ideally, the patient's body would provide both the source of cells and the environment for terminal differentiation, provided the appropriate cues can be mediated through the biomaterial. In contrast to current modalities that focus on in vitro manipulation of cells, the invention provides methods for controlling tissue morphogenesis in vivo by providing the appropriate cues to infiltrating multipoint cells, leading to the production of functional tissues in situ.

The invention also pertains to regenerating or augmenting tissue and/or organ function by recruiting native stem cells to a target site by delivering a biocompatible substance to a target site. Biocompatible refers to materials that do not have toxic or injurious effects on biological functions. Biodegradable refers to material that can be absorbed or degraded in a patient's body. Representative materials for forming the biodegradable material include natural or synthetic polymers, such as, collagen, poly(alpha esters) such as poly (lactic acid), poly(glycolic acid), polyorthoesters and polyanhydrides and their copolymers, which degraded by hydrolysis at a controlled rate and are reabsorbed. These materials provide the maximum control of degradability, manageability, size and configuration. Preferred biodegradable polymer materials include polyglycolic acid and polyglactin, developed as absorbable synthetic suture material.

Polyglycolic acid and polyglactin fibers may be used as supplied by the manufacturer. Other biodegradable materials include, but are not limited to, cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, or copolymers or physical blends of these materials. The material may be impregnated with suitable antimicrobial agents and may be colored by a color additive to improve visibility and to aid in surgical procedures.

The polymers can be characterized for mechanical properties such as tensile strength using an Instron tester, for polymer molecular weight by gel permeation chromatography (GPC), glass transition temperature by differential scanning calorimetry (DSC) and bond structure by infrared (IR) spectroscopy; with respect to toxicology by initial screening tests involving Ames assays and in vitro teratogenicity assays, and implantation studies in animals for immunogenicity, inflammation, release and degradation studies. In vitro cell attachment and viability can be assessed using scanning electron microscopy, histology, and quantitative assessment with radioisotopes.

In some embodiments, the biocompatible substrate can be shaped using methods such as, solvent casting, compression molding, filament drawing, meshing, leaching, weaving and coating. In solvent casting, a solution of one or more polymers in an appropriate solvent, such as methylene chloride, is cast as a branching pattern relief structure. After solvent evaporation, a thin film is obtained. In compression molding, the substrate is pressed at pressures up to 30,000 pounds per square inch into an appropriate pattern. Filament drawing involves drawing from the molten polymer and meshing involves forming a mesh by compressing fibers into a felt-like material. In leaching, a solution containing two materials is spread into a shape close to the final form of the tissue. Next a solvent is used to dissolve away one of the components, resulting in pore formation. (See Mikos, U.S. Pat. No. 5,514,378, hereby incorporated by reference).

Thus, the substrate can be shaped into any number of desirable configurations to satisfy any number of overall system, geometry or space restrictions. The biomaterial can be shaped to different sizes to conform to the necessary structures of different sized patients.

A substrate can also be permeated with a material, for example liquefied copolymers (poly-DL-lactide co-glycolide 50:50 80 mg/ml methylene chloride) to alter its mechanical properties. This can be performed by coating one layer, or multiple layers until the desired mechanical properties are achieved.

In one embodiment, the biomaterial is an injectable biomaterial that can be composed of crosslinked polymer networks which are typically insoluble or poorly soluble in water, but can swell to an equilibrium size in the presence of excess water. For example, the hydrogel can be injected into desired locations within the organ. In one embodiment, the collagen can be injected alone. In another embodiment, the collagen can be injected with other hydrogels. The hydrogel compositions can include, without limitation, for example, poly(esters), poly(hydroxy acids), poly(lactones), poly(amides), poly(ester-amides), poly(amino acids), poly(anhydrides), poly(ortho-esters), poly(carbonates), poly(phosphazines), poly(thioesters), polysaccharides and ' mixtures thereof. Furthermore, the compositions can also include, for example, a poly(hydroxy) acid including poly(alpha-hydroxy) acids and poly(beta-hydroxy) acids. Such poly(hydroxy) acids include, for example, polylactic acid, polyglycolic acid, polycaproic acid, polybutyric acid, polyvaleric acid, and copolymers and mixtures thereof. Due to the unique properties of hydrogels and their potential applications in such areas as controlled drug delivery, various types of hydrogels have been synthesized and characterized.

The bulk polymerization, i.e., polymerization in the absence of added solvent, of monomers to make a homogeneous hydrogel produces a glassy, transparent polymer matrix which is very hard. When immersed in water, the glassy matrix swells to become soft and flexible. Porous hydrogels are usually prepared by a solution polymerization technique, which entails polymerizing monomers in a suitable solvent. The nature of a synthesized hydrogel, whether a compact gel or a loose polymer network, depends on the type of monomer, the amount of diluent in the monomer mixture, and the amount of crosslinking agent. As the amount of diluent (usually water) in the monomer mixture increases, the pore size also increases up to the micron range. Hydrogels with effective pore sizes in the 10-100 nm range and in the 100 nm-10 micrometer range are termed "microporous" and "macroporous" hydrogels, respectively. The microporous and macroporous structures of hydrogels can be distinguished from those of non-hydrogel porous materials, such as porous polyurethane foams. In the plastic foam area, micro- and macro-pores are indicated as having pores less than 50 micrometers and pores in the 100-300 micrometer range, respectively. One of the reasons for this difference is that hydrogels with pores larger than 10 micrometers are uncommon, while porous plastics having pores in the 100-300 micrometer range are very common.

Microporous and macroporous hydrogels are often called polymer "sponges." When a monomer, e.g., hydroxyethyl methacrylate (HEMA), is polymerized at an initial monomer concentration of 45 (w/w) % or higher in water, a hydrogel is produced with a porosity higher than the homogeneous hydrogels. Hydrogels can also expand in the presence of diluent (usually water). The matrix materials of present invention encompass both conventional foam or sponge materials and the so-called "hydrogel sponges." For a further description of hydrogels, see U.S. Pat. No. 5,451,613 (issued to Smith et al).

Collagen gels can also be used. The collagen used in the present invention can be collagen such as Type I, Type III or Type I+III collagen, for example, alkaline treatment of insoluble collagen extracted from various animals, or by treating with enzyme such as pepsin, trypsin, chymotrypsin, papain or pronase. There are no particular restrictions on the origin of the collagen, and typically collagen can be used that is obtained from the skin, bone, cartilage, tendon or organs, etc. of birds or mammals such as cows, pigs, rabbits, sheep and mice. Since collagen allows the obtaining of a suitable consistency without heating, preparation can be made easily in the case of gelation. In addition, collagen has a high molecular weight, it more closely resembles living body tissue, has considerable physiological activity, and therefore promotes healing in the case of using on a wound, resulting in a favorable effect for tissue regeneration. Collagen can be flexible after curing and requires only a short time for crosslinking, in other words, requires only a short time for gelation. Collagen solution can also be made by dissolving in a non-toxic solvent with respect to the living body, examples of which include water, physiological saline, a buffer such as borate buffer, or an aqueous solution containing a salt such as sodium chloride, sodium bromide and potassium bromide, or protein, sugar or lipid, etc.

The collagen can also form a gel even in the presence of moisture such as that in blood or humor, and can demonstrate a high degree of adhesiveness with respect to living body tissue. Collagen solutions used in the present invention can be made at various concentrations, neutralized and prepared for injection. Preferably, collagen at 0.2 mg/mL, 0.5 mg/ml, 0.75 mg/ml, 1 mg/ml, 2 mg/ml, 3 mg/ml, 4 mg/ml, 5 mg/ml, 6 mg/ml, 7 mg/ml, 8 mg/ml, 10 mg/ml, 20 mg/ml, 30 mg/ml, 40 mg/ml and 5 mg/ml in solution can be used for injection. More preferably, collagen concentration from about 1 mg/ml to about 30 mg/ml solution can be used for injection. Upon injection into an organ, chilled collagen gels can thermogel as they reached body temperature or about 37° C.

The biocompatible substance can also have a range of viscosities. In some aspects, the biocompatible substance has a viscosity between about 5 cP to about $1\times10^8$ cP, or about 5 cP to about $1\times10^6$ cP, or about 5 cP to about $1\times10^5$ cP, or about 5 cP to about $1\times10^4$ cP, or about 10 cP to about $1\times10^3$ cP, or about 6 cP to about 9500 cP at 25° C.

III. Adjuvants

Substrates can be treated with additives or drugs prior to implantation (before or after the polymeric substrate is seeded with cells), e.g., to enhance native stem cell recruitment, and differentiation into new tissue after implantation. Thus, for example, growth factors, cytokines, extracellular matrix components, and other bioactive materials can be added to the substrate to promote graft healing and formation of new tissue. Such additives will in general be selected according to the tissue or organ being reconstructed or augmented, to ensure that appropriate new tissue is formed in the engrafted organ or tissue (for examples of such additives for use in promoting bone healing, see, e.g., Kirker-Head, C. A. Vet. Surg. 24 (5): 408-19 (1995)). For example, vascular endothelial growth factor (VEGF, see, e.g., U.S. Pat. No. 5,654,273 herein incorporated by reference) can be employed to promote the formation of new vascular tissue. Growth factors and other additives (e.g., epidermal growth factor (EGF), heparin-binding epidermal-like growth factor (HBGF), fibroblast growth factor (FGF), cytokines, genes, proteins, and the like) can be added in amounts in excess of any amount of such growth factors (if any) which may be produced by the cells seeded on the substrate. Such additives are preferably provided in an amount sufficient to promote the formation of new tissue of a type appropriate to the tissue or organ, which is to be repaired or augmented (e.g., by causing or accelerating infiltration of host cells into the graft). Other useful additives include antibacterial agents such as antibiotics.

The substrate can also be treated or seeded with various factors and proteins to control the degradation/absorption of the biomaterial in the subject. For instance, if the cells recruited to the biomaterial are slow-growing, then it is beneficial to maintain the biomaterial integrity for a long enough period of time to allow the cells enough time to regenerate and grow. On the other hand, if the cells are able to quickly reproduce and grow, then a short lived substrate could be desirable. Varying the concentration of aprotinin additives, aminocaproic acid, tranxemic acid, or similar fibrinolytic inhibitors or the degree of chemical cross-linking in the biomaterial could be used to precisely control this variable. The substrate could also be seeded with varying growth factors.

A person skilled in the art will appreciate that the biocompatible substances can have a variety of other configurations and can include various other features known in the art. In some embodiments, the biocompatible substance of the present invention can also be used with suitable adjuvants for improving the target site for in situ tissue regeneration. As such the invention extends to compositions as previously defined, additionally comprising one or more adjuvants. For example, non-limiting suitable adjuvants include the general classes of: antibacterial agents, such as metronidazole, silver; anaesthetic/analgesics, such as lidocaine, benzovaine; anti-inflammatory agents, such as steroidal, non-steroidal; collagen synthetase inhibitors, growth factors, such as transforming growth factor beta, endothelial growth factor, basic fibroblast growth factor, nerve growth factor; enzymes for debridement, such as subtilysin, bromain, papain; and genes for gene therapy, such as the vascular endothelial GF-2 (VEGF) angiogenesis gene. In some embodiments, one or more anti-inflammatory agents can be delivered to the target site, and/or incorporated into the biocompatible substance. In preferred embodiments, the anti-inflammatory agent is a collagen reducing agent. Anti-inflammatory agents can be steroidal or non-steroidal. Non-limiting examples of anti-inflammatory agents include; corticosteroids, dexamethasone, collagenase, rapamycin, paclitaxel, ABT-578, everolimus, taxol, steroidal anti-inflammatory agents, non-steroidal anti-inflammatory agents, hemostatic agents; antimicrobial agents; antibiotics; antifungals; antiprotozoals; antivirals; antimicrobial metals; hemostatic and/or vasoconstricting agents; pseudoephedrine; xylometazoline; oxymetazoline; phenylephrine; epinephrine; cocaine; local anesthetic agents; lidocaine; cocaine; bupivacaine; hormones; hormonally active agents; agents that enhance potency; substances that dissolve, degrade, cut, break, weaken, soften, modify or remodel connective tissue or other tissue; enzymes; trypsin; EDTA; trypsin combined with EDTA; hyaluronidase; tosyllysylchloromethane (TLCM)); chemotherapeutic or antineoplastic agents; substances that prevent adhesion formation; hyaluronic acid gel. Non-limiting examples of collagen synthetase inhibitors include collagenase, halofuginone, propyl hydroxylase, c-proteinase inhibitor, and metalloproteinase. It will be appreciated that other suitable compounds can be used, as appropriate.

Adjuvants can be any suitable therapeutic or biological agent such as genetic material, growth factors, cytokines, enzymes. The adjuvant can also be released at a specific site as a function of biodegradation of the biomaterial in the surrounding environment over time.

Examples of adjuvants include, but are not limited to proteins growth factors, antibodies, nucleic acids molecules, carbohydrates, anti-inflammatory agents, and the like. Growth factors useful in the present invention include, but are not limited to, transforming growth factor-alpha (TGF-α), transforming growth factor-beta (TGF-β), platelet-derived growth factors (PDGF), fibroblast growth factors (FGF), including FGF acidic isoforms 1 and 2, FGF basic form 2 and FGF 4, 8, 9 and 10, nerve growth factors (NGF) including NGF 2.5 s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), granulocyte colony stimulating factor (G-CSF), insulin like growth factor (IGF) I and II, hepatocyte growth factor, glial neurotrophic growth factor (GDNF), stem cell factor (SCF), keratinocyte growth factor (KGF), transforming growth factors (TGF), including TGFs alpha, beta, beta1, beta2, beta3, skeletal growth factor, bone matrix derived growth factors, and bone derived growth factors and mixtures thereof.

Cytokines useful in the present invention include, but are not limited to, cardiotrophin, stromal cell derived factor, macrophage derived chemokine (MDC), melanoma growth stimulatory activity (MGSA), macrophage inflammatory proteins 1alpha (MIP-1 alpha), 2, 3 alpha, 3 beta, 4 and 5, IL-1, IL-2, IL-3, IL-4, IL-5, IL-6, IL-7, IL-8, IL-9, IL-10, IL-11, IL-12, IL-13, TNF-alpha, and TNF-beta. Immunoglobulins useful in the present invention include, but are not limited to, IgG, IgA, IgM, IgD, IgE, and mixtures thereof. Some preferred growth factors include VEGF (vascular endothelial growth factor), NGFs (nerve growth factors), PDGF-AA, PDGF-BB, PDGF-AB, FGFb, FGFa, and BGF.

In some embodiments, one or more anti-inflammatory agents can be delivered to the target site, and/or incorporated into the biocompatible substance. In preferred embodiments, the anti-inflammatory agent is a collagen reducing agent. Anti-inflammatory agents can be steroidal or non-steroidal. Non-limiting examples of anti-inflammatory agents include, corticosteroids, dexamethasone, collagenase, rapamycin, paclitaxel, ABT-578, everolimus, taxol, steroidal anti-inflammatory agents, non-steroidal anti-inflammatory agents, hemostatic agents; antimicrobial agents; antibiotics; antifungals; antiprotozoals; antivirals; antimicrobial metals; hemostatic and/or vasoconstricting agents; pseudoephedrine; xylometazoline; oxymetazoline; phenylephrine; epinephrine; cocaine; local anesthetic agents; lidocaine; cocaine; bupivacaine; hormones; hormonally active agents; agents that enhance potency; substances that dissolve, degrade, cut, break, weaken, soften, modify or remodel connective tissue or other tissue; enzymes; trypsin; EDTA; trypsin combined with EDTA; hyaluronidase; tosyllysylchloromethane (TLCM)); chemotherapeutic or antineoplastic agents; substances that prevent adhesion formation; hyaluronic acid gel. Non-limiting examples of collagen synthetase inhibitors include collagenase, halofuginone, propyl hydroxylase, c-proteinase inhibitor, and metalloproteinase. It will be appreciated that other suitable compounds may be used, as appropriate.

Other molecules useful as therapeutic or biological agents include, but are not limited to, growth hormones, leptin, leukemia inhibitory factor (LIF), endostatin, thrombospondin, osteogenic protein-1, bone morphogenetic proteins 2 and 7, osteonectin, somatomedin-like peptide, osteocalcin, interferon alpha, interferon alpha A, interferon beta, interferon gamma, interferon 1 alpha.

Embodiments involving amino acids, peptides, polypeptides, and proteins may include any type or combinations of such molecules of any size and complexity. Examples include, but are not limited to structural proteins, enzymes, and peptide hormones. These compounds can serve a variety of functions. In some embodiments, the biomaterial can contain peptides containing a sequence that suppresses enzyme activity through competition for the active site. In substances such as nucleic acids, any nucleic acid can be present. Examples include, but are not limited to deoxyribonucleic acid (DNA), and ribonucleic acid (RNA). Embodiments involving DNA include, but are not limited to, cDNA sequences, natural DNA sequences from any source, and sense or anti-sense oligonucleotides. For example, DNA can be naked (e.g., U.S. Pat. Nos. 5,580,859; 5,910,488) or complexed or encapsulated (e.g., U.S. Pat. Nos. 5,908,777; 5,787,567). DNA can be present in vectors of any kind, for example in a viral or plasmid vector. In some embodiments, nucleic acids used will serve to promote or to inhibit the expression of genes in cells recruited inside to the biomaterial. The nucleic acids can be in any form that is effective to enhance its uptake into cells.

The state of the biomaterial in relation to the adjuvant can be controlled by the coupling chemistry, whether the therapeutic/biological agent is encapsulated, the selection of biomaterial compounds, solvent(s), and solubility of the biomaterial compounds in those solvents. These parameters can be manipulated to control the release of the therapeutic/biological agents. It is to be understood that the adjuvant can be entrapped or entangled within a biomaterial, bonded to a biomaterial, contained within cavities, enclosures, inclusions, or pockets, or structures of a biomaterial (e.g. fibers, fibrils, particles) or externally bound to the biomaterial.

In particular, the adjuvant can be entrapped or encapsulated to produce "nanocapsules." These nanocapsules containing the adjuvant can be produced by standard encapsulating techniques. Microencapsulation of adjuvants generally involve three steps: (a) generating microcapsules enclosing the adjuvant (e.g., by forming droplets of cell-containing liquid alginate followed by exposure to a solution of calcium chloride to form a solid gel), (b) coating the resulting gelled spheres with additional outer coatings (e.g., outer coatings comprising polylysine and/or polyornithine) to form a semipermeable membrane; and (c) liquefying the original core gel (e.g., by chelation using a solution of sodium citrate). The three steps are typically separated by washings in normal saline.

Another method of microencapsulating adjuvants can be the alginate-polyamino acid technique. Droplets of sodium alginate are produced. Droplets of alginate flow into calcium chloride in saline. The negatively charged alginate droplets bind calcium and form a calcium alginate gel. The microcapsules are washed in saline and incubated with poly-L-lysine (PLL) or poly-L-ornithine (or combinations thereof); the positively charged poly-l-lysine and/or poly-L-ornithine displaces calcium ions and binds (ionic) negatively charged alginate, producing an outer poly-electrolyte membrane. A final coating of sodium alginate may be added by washing the microcapsules with a solution of sodium alginate, which ionically bonds to the poly-L-lysine and/or poly-L-ornithine layer. See U.S. Pat. No. 4,391,909 to Lim et al (all U.S. patents referenced herein are intended to be incorporated herein in their entirety). This technique produces what has been termed a "single-wall" microcapsule. Preferred microcapsules are essentially round, small, and uniform in size. (Wolters et al., *J. Appli Biomater.* 3:281 (1992)).

The alginate-polylysine microcapsules can also then be incubated in sodium citrate to solubilize any calcium alginate that has not reacted with poly-1-lysine, i.e., to solubilize the internal core of sodium alginate, thus producing a microcapsule with a liquefied core portion. See Lim and Sun, Science 210:908 (1980). Such microcapsules are referred to herein as having "chelated", "hollow" or "liquid" cores. A "double-wall" microcapsule is produced by following the same procedure as for single-wall microcapsules, but prior to any incubation with sodium citrate, the microcapsules are again incubated with poly-l-lysine and sodium alginate.

Many alternative techniques used for encapsulating different agents are known in the art and can be used with this invention. U.S. Pat. No. 5,084,350 discloses microcapsules enclosed in a larger matrix, where the microcapsules are liquefied once the microcapsules are within the larger matrix. Tsang et al., U.S. Pat. No. 4,663,286 discloses encapsulation using an alginate polymer, where the gel layer is cross-linked with a polycationic polymer such as polylysine, and a second layer formed using a second polycationic polymer (such as polyornithine); the second layer can then be coated by alginate. U.S. Pat. No. 5,762,959 to Soon-Shiong et al. discloses a microcapsule having a solid (non-chelated) alginate gel core of a defined ratio of calcium/barium alginates, with polymer material in the core. U.S. Pat. Nos. 5,801,033 and 5,573,934 to Hubbell et al. describe alginate/polylysine microspheres having a final polymeric coating (e.g., polyethylene glycol (PEG)); Sawhney et al., Biomaterials 13:863 (1991) describe alginate/polylysine microcapsules incorporating a graft copolymer of poly-1-lysine and polyethylene oxide on the microcapsule surface, to improve biocompatibility; U.S. Pat. No. 5,380,536 describes microcapsules with an outermost layer of water soluble non-ionic polymers such as polyethylene(oxide). U.S. Pat. No. 5,227,298 to Weber et al. describes a method for providing a second alginate gel coating to cells already coated with polylysine alginate; both alginate coatings are stabilized with polylysine. U.S. Pat. No. 5,578,314 to Weber et al. provides a method for microencapsulation using multiple coatings of purified alginate. U.S. Pat. No. 5,693,514 to Dorian et al. reports the use of a non-fibrogenic alginate, where the outer surface of the alginate coating is reacted with alkaline earth metal cations comprising calcium ions and/or magnesium ions, to form an alkaline earth metal alginate coating. The outer surface of the alginate coating is not reacted with polylysine. U.S. Pat. No. 5,846,530 to Soon-Shiong describes microcapsules containing cells that have been individually coated with polymerizable alginate, or polymerizable polycations such as polylysine, prior to encapsulation.

An adjuvant can be coupled to a nanoparticle and release kinetics of the adjuvant can be controlled. One skilled in the art will appreciate that the control release kinetics depend on the capsulation parameters including nanocapsule size, adjuvant loading, and polymer composition. The mean diameter of the nanocapsules depends on the mixing velocity of the preparation process and viscosity of the preparation media. Nanocapsule size can be reduced by exposing the preparation to sonication over a range of about 30 second to about 120 seconds, increasing the sonication intensity from about 5 watts to about 20 watts, or by varying the ratios of organic polymer phase to aqueous phase. Nanocapsule sizes can be characterized by scanning electron microscopy (SEM), coulter counter, and light scattering.

For polymer encapsulation, FDA approved biodegradable polymers (PLA, PLGA, PCL) can be used for the control of encapsulation and degradation of the nanocapsules in vivo.

In one embodiment, the adjuvant can be joined to the biomaterial by peptide bonds. For example, nanoparticles can be incorporated into the biomaterial using EDC (1-ethyl-3(3-dimethyl aminopropyl) carbodiimide) and sulfo-NHS (N-hydrocyl-sulfo-succinimide) to form peptide bonds. Various other know techniques can be used as described, for example, in Heumanson, Bioconjugate Techniques, Academic Press San Diego, Calif., 1996, herein incorporated by reference. For external incorporation, a peptide bond can be created between the biomaterial and the adjuvant using the EDC/sulpho-NHS method to form peptide bonds between the carboxylates and amino groups. The adjuvant can also be added internally to the biomaterial by incorporating each component into the solution with at least one natural compound and at least one synthetic compound.

Examples of some possible chemistries of incorporating agents include, but are not limited to, esterification (e.g., with acyl halides, acid anhydrides, carboxylic acids, or esters via interchange reactions), ether formation (for example, via the Williamson ether synthesis), urethane formation via reactions with isocyanates, sulfonation with, for example, chlorosulfonic acid, and reaction of b-sulfatoethylsulfonyl aniline to afford an amine derivative that can be converted to a diazo for reaction with a wide variety of compounds. Such chemistries can be used to attach a wide variety of substances to the biomaterial, including but not limited to crown ethers (Kimura et al., (1983) *J. Polym. Sci.* 21, 2777), enzymes (Chase et al. (1998) *Biotechnol. Appl. Biochem.*, 27, 205), and nucleotides (Overberger et al. (1989) *J. Polym. Sci.* 27, 3589).

IV. Injection and Implantation of Biomaterials

The substantially cell-free biomaterial can be implanted or injected into an organ requiring regeneration or organ augmentation using standard surgical procedures. These surgical procedures may vary according to the organ being augmented. For kidney implantation, it may be desirable to implant a series of substantially cell-free biomaterials into incisions formed along the avascular plane of the kidney, or the least vascular region of an organ. In other applications, the constructs of the invention can be introduced by less invasive procedures, e.g., via a cannula, needle, trocar or catheter-type instrument.

A person skilled in the art will appreciate that the biocompatible substance can be delivered/implanted by a variety of methods known in the art. Other embodiments and uses of the invention will be apparent to those skilled in the art from consideration of the specification and practice of the invention disclosed herein. All U.S. Patents and other references noted herein for whatever reason are specifically incorporated by reference. The specification and examples should be considered exemplary only with the true scope and spirit of the invention indicated by the claims.

EXAMPLES

The examples demonstrate that host cell infiltrates into a biomaterial implant are not entirely comprised of inflammatory and fibroblast-like cells, and that normal inflammatory process can be altered by incorporating agents that influence environmental cues. The infiltrated cells are capable of differentiating into multiple cell lineages if appropriate conditions are provided. It is possible to recruit a predominance of native cells with multilineage potential into a biomaterial scaffold. Therefore, it is possible to enrich the infiltrate with such cell types and control their fate, provided the proper substrate-mediated signaling can be imparted into the scaffold.

Example 1: Methods and Materials

Normal Mouse Model

All animal procedures were performed in accordance with a protocol approved by the institutional Animal Care and Use Committee (ACUC) at Wake Forest University. CD1 mice (6-8 weeks) were purchased from Charles River Laboratories Inc. (Wilmington, Mass.). Under anesthesia using isoflurane, the kidneys were accessed through a dorsal incision and then collagen gels were injected into kidneys. Mice were divided into three experimental groups (n=20 per time point). The following treatments were administered via multiple injections into both kidneys using a 22-gauge needle: (1) collagen gel (0.2% wt/vol, 50 nL/kidney), (2) saline (0.9% NaCl, 50 uL/kidney, Hospira, Inc, Lake Forest, Ill.), and (3) needle sticks only. Sham operation served as a control. The kidneys were harvested at 1, 2, 3, and 4 weeks after injection for histological and immunohistochemical analyses Collagen Gel Preparation Rat tail type I collagen solution was obtained from BD Biosciences (Franklin Lakes, N.J.). Collagen gels were prepared on ice. Briefly, collagen solution (0.2% wt/vol) was neutralized by adding IN NaOH solution to give a final pH of 7.4. Neutralized collagen gels were tested to achieve optimal injection conditions prior to injection. Upon injection into the kidney, the collagen gels thermogelled as they reached 37° C. All chemicals were obtained from Sigma-Aldrich Co. (St Louis, Mo.) and used as received unless stated otherwise.

Renal Ischemia/Reperfusion Rat Model

Seventy Lewis rats (6-8 weeks, weight approximately 200 g, Charles River Laboratories Inc.) were anesthetized with an intraperitoneal injection of sodium pentobarbital (Nembutal, Ovation Pharmaceuticals, Inc., Deerfield, Ill.) at an initial dose of 50 mg/kg. If necessary, anesthesia was maintained using a second 25 mg/kg dose. The kidneys were exposed through a 3 cm midline abdominal incision. The bilateral renal pedicles were isolated. Each renal artery and vein was occluded with non-traumatic clamps (Micro-serrefine curved 6 mm, Fine Science Tools Inc. Foster, Calif.) for 60 min. At the end of this time period, the clamps were released to allow renal reperfusion. The abdominal wall was closed in two layers. Post surgical pain was managed with buprenorphine (Reckitt Benckiser Pharmaceuticals, Richmond, Va., 0.05 mg/Kg subcutaneously). Three weeks after ischemia/reperfusion surgery, a neutralized collagen gel (0.2% wt/vol, 400 uL) was injected into multiple areas of the kidneys using a 20-gauge needle. Sham operation and saline injection groups served as controls as described above.

Scaffold Implantation

Nonwoven poly(glycolic acid) (PGA; density 50 mg/cc, thickness 2 mm) was used as a polymeric scaffold to accommodate host cell infiltration and was obtained from Biomedical Structures, Inc. (Slaterville, R.I., USA). All chemicals were obtained from Sigma-Aldrich Co. (St Louis, Mo., USA) and used as received unless stated otherwise.

In a separate set of experiments, dexamethasone, which is a known anti-inflammatory agent, was incorporated into the PGA scaffolds to determine whether normal host tissue response could be altered. PGA scaffolds (8*8×2 mm) were treated with dexamethasone (0.2 mg/mL)-loaded Pluronic F127 hydrogel. The scaffolds 1 were implanted subcutaneously under the dorsal skin of CD1 mice, and retrieved at 3 and 4 weeks after implantation. PGA scaffolds with Pluronic F127 hydrogel only served as controls. The retrieved scaffolds were assessed for DNA and soluble collagen content.

Scanning Electron Microscope (SEM)

Morphology of the implanted PGA scaffolds was examined by SEM (Model S-2260N, Hitachi Co. Ltd., Tokyo, Japan). Samples were observed under an environmental SEM (backscatter electron mode) without any conductive coating. To observe morphologies, samples were fixed with 1% glutaraldehyde solution and dehydrated through a series of graded ethanol solutions, followed by observation with SEM.

Measurement of Cellular Component in Implants

Retrieved scaffolds were fixed in 10% buffered formalin, sectioned, and stained with hematoxylin and eosin (H&E). The number of infiltrating cells was counted in representative sections. Cell numbers were measured in each section using nine randomly selected neighboring fields of equal area and averaged. Counts were expressed as average number per $mm^2$.

Retrieved scaffolds were also analyzed for DNA content. The DNA was purified using DNeasy® kit (QIAGEN Inc., Valencia, Calif., USA) and concentration was measured by spectrophotometric analysis (BioMate 3, Thermo Electron Corporation, Waltham, Mass., USA).

Measurement of Collagen Content

Collagen content was assessed with Masson's trichrome staining. Retrieved scaffolds were fixed in 10% buffered formalin and Bouin's fixation solution and sectioned. The slides were placed in Weigert's iron hematoxylin working solution followed by rinse with water. Subsequently, the slides were placed in Biebrich Scarlet-acid fuchsin, incubated with phosphotungstic-phosphomolybdic acid and stained with aniline blue. Photomicrographs were taken using a Nikon light microscope.

The retrieved scaffolds were quantitatively analyzed for total collagen content. Total soluble collagen was extracted using 1 mg/ml pepsin in 0.5 M acetic acid for 72 hr at 4° C. The samples were centrifuged and supernatants stored for further analysis. The collagen concentration was measured using a Sircol™ Soluble Collagen Assay kit (Biocolor Ltd., Belfast, Northern Ireland) according to the manufacturer's instructions. The dye in the kit binds specifically to the sequence $[Gly-X-Y]_n$ present in all collagen types. Collagen content was normalized to the implanted scaffold wet weight.

Culture of Infiltrating Cells

The implanted PGA scaffolds were retrieved at their predetermined time points. The infiltrating cells were isolated by cutting the scaffolds into small pieces (1 $mm^3$), and digesting in sterile phosphate-buffered saline containing 1.25 mg/ml collagenase type I (Worthington Biochemical Corporation, Lakewood, N.J., USA) for 2 hr at 37° C. The cells were resuspended in culture medium, plated on tissue culture dishes and grown to confluence for 2-3 weeks at 5% $CO_2$, 95% humidity and 37° C. Unless indicated otherwise, original culture medium consisted of low-glucose Dulbecco's modified Eagle medium (DMEM) supplemented with 10% fetal bovine serum (FBS) and 1% penicillin/streptomycin. The cells were subcultured using 0.25% trypsin containing 1 raM EDTA for 5 min at 37° C. All cells were cultured at 5% $CO_2$, 37° C., and 95% humidity unless otherwise indicated.

FACS Analysis and IF Staining

Fluorescence-activated cell scanning (FACS) analysis was performed for CD34, CD45, CD90, Sca-1, and Flk-1. For all antibodies, $0.5 \times 10^6$ of the infiltrating cells were incubated in 100 uL of PBS containing 1% FBS and primary antibody at dilutions ranging from 1:15 to 1:100. Cells were incubated with primary antibody on ice for 30 min, washed with 1% FBS in PBS, resuspended in 100 ul of fluorescein isothiocyanate (FITC)-labeled secondary antibody, diluted 1:100 in 1% FBS in PBS, and incubated for an additional 30 min on ice. The cells were then washed with PBS containing 1% FBS, and resuspended in PBS with 1% FBS for FACS analysis. Isotype-matching immunoglobulin (IgG) and FITC-labeled secondary antibody were used to determine nonspecific signals. FACS analyses were performed with a FACSCalibur flow cytometer (BD FACSCalibur System, San Jose, Calif., USA) equipped with an air cooled argon laser (588-nm emission). The infiltrating cells were also characterized by immunofluorescent (IF) staining using anti-CD34 and rat anti-mouse Sca-1 (1:200, BD Biosciences Pharmingen, San Diego, Calif.) as the primary antibodies. Samples were incubated with primary antibody for 1 hr at room temperature with subsequent washing in PBS followed by incubation with the secondary antibody (FITC-conjugated horse antibody to mouse IgG, 1:500, DakoCytomation, Carpinteria, Calif., USA) for 30 min. After IF staining, the cells were viewed using a fluorescence microscope (Nikon, Japan). Samples stained without primary antibody served as a negative control.

Multilineage Differentiation: Oxteosenic Induction

To determine whether infiltrating cells could undergo osteogenic differentiation, cells at passage four were plated at a density of 5,000 cells/$cm^2$ and cultured in low-glucose DMEM medium with 10% FBS, 1% penicillin/streptomycin, osteogenic supplements (100 nM dexamethasone, 10 mM β-glycerophosphate and 0.05 mM ascorbic acid-2-phosphate). As a control, cells were also cultured in the original culture medium. The cells were cultured in osteogenic medium for up to 30 days with media changes every 3 days.

Cellular mineralization was determined by von Kossa staining. The cells were fixed with 10% formaldehyde, incubated with 2% silver nitrate solution for 10 min, washed with deionized water, and exposed to UV light for 15 min.

Endothelial Induction

For the induction of endothelial differentiation, passage four cells were plated at a density of 5,000 cells/$cm^2$ and subsequently cultured in EGM-2 (Endothelial growth medium-2, CAMBREX, Walkersville, Md., USA) culture media. The cells were sub-cultured on 6-well tissue culture plates coated with Matrigel™ (BD Biosciences, Bedford, Mass., USA) to assess capillary formation. After allowing 30 minutes after initial seeding for cell attachment, EGM-2 was added. Twelve hours later, the cells were examined under a phase-contrast microscope (Nikon, Japan) for evidence of capillary formation.

Adipogenic Induction

For induction of adipogenic differentiation, passage four cells were plated at a density of 5,000 cells/$cm^2$, allowed to adhere, and cultured after submersion in low-glucose DMEM supplemented with 10% FBS, 1% penicillin/streptomycin, and adipogenic supplements (1 μM dexamethasone, 1 mM 3-isobutyl-1-methylxanthine, 10 μg/ml insulin and 60 μM indomethacin). The cells cultured in the original culture medium served as a control. The medium was changed every 3 days.

The presence of intracellular lipid vacuoles was determined with Oil-Red-O. The cells were incubated with Oil-Red-O staining solution, rinsed with 50% ethanol, 2 rinsed again with distilled water, counterstained with Gill's hematoxylin, rinsed in deionized water and mounted with water-based mounting media.

Myogenic Induction

For the induction of myogenic differentiation, passage four cells were plated at a density of 5,000 cells/$cm^2$ on dishes and cultured with myogenic media (low-glucose DMEM supplemented with 10% horse serum, 0.5% chick embryo extract and 1% penicillin/streptomycin). After a 12-hr equilibration period, 5-azacytidine (10 μM) was added for 24 hr and then the media was replaced with 5-azacytidine-free medium. As a control, some cells were cultured in the original culture medium. Culture medium was changed every 3 days.

Immunohistochemical Analyses

The differentiated cells were detected by anti-osteocalcin antibodies (Santa Cruz Biotechnology, Inc., Santa Cruz, Calif., USA) for osteogenic induction, anti-PECAM-1 and anti-von Willebrand factor (vWF) for endothelial induction, and anti-a-smooth muscle actin and anti-desmin for myogenic induction.

Briefly, the differentiated cells in 6-well plates were fixed with cold ethanol (−20° C.). Nonspecific protein binding was blocked with 10% serum in PBS for 1 hr at room temperature, and cells subsequently incubated with primary antibody overnight at 4° C. The cells were washed thoroughly with PBS and incubated with FITC-conjugated secondary antibody for 1 hr at room temperature. The cell were washed with PBS and mounted with a solution containing DAPI to detect nuclei (VectaShield, Vector Labs, Burlingame, Calif., USA).

Identification of Host Cells

In order to examine the infiltrating host cells into the injection regions, immunohistochemical staining for bromodeoxyuridine (BrdU) and proliferating cell nuclear antigen (PCNA, Dako) was performed as described above. For BrdU labeling, BrdU (100 mg/kg) was injected intraperitoneally into normal CD1 mice daily for 2 weeks.

Quantitative analysis of PCNA-positive cells was performed by counting the 2 positive nuclei in injection and normal regions from five randomly selected fields under a light microscope at magnification ×200.

Characterization of Newly Formed Renal Tissues

The regenerated renal structures were identified by immunohistochemistry with cell specific markers: mouse anti-human CD31 (Dako), mouse anti-rat synaptopodin (Fitzgerald industries International, Concord, Mass.), cytokeratin (Dako), and polyclonal rabbit anti-neprilysin (1:100, Millipore, Billerica, Mass.). To quantify the effects of the injection of collagen gel, the number of glomeruli in the injection regions and normal regions was counted and quantified.

Functional Testing

Blood samples for creatinine and blood urea nitrogen (BUN) determination were collected. Briefly, blood samples were collected from rat tail artery at weekly intervals from 1 week before ischemia/reperfusion injury until 3 weeks after surgery for all the rats. Serum creatinine and BUN were measured using an automatic modular analyzer (Synchron CX5 delta, Beckman Coulter Inc., Brea, Calif.).

Positive Pressure Measurement During the Injection

Animals (mice and rats) were anesthetized using 3% isoflurane in 100% oxygen via nasal cannel. The 22 gauge needle and the sensor from pressure transducer (blunt 26 gauge needle, pressure transducer from ADInstrument Inc. Colorado Spring, Colo.) were fixed together and the tip of the needle and the sensor was at the same level. After laparotomy, saline (0.9% NaCl, 0.4 ml, Abbot Inc.) and collagen (1, 2, and 5 mg/ml, 0.4 ml per injection, BD Biosciences, Bedford, Mass.) was injected into the low pole renal parenchyma through 22 gauge needle (N=3 kidneys per concentration). The pressure during injection was recorded via data acquisition system (PowerLab 8/30, ADInstrument Inc. Colorado Spring, Colo.).

Space

Mice were anesthetized using 3% isoflurane in 100% oxygen via nasal cannel. The kidney was approached through laparotomy. A space-specific lesion was made using 2 mm biopsy punch (Miltrex Inc., York, Pa.) at the low pole of each kidney. The hole was about 2 mm depth. After removed the renal tissue from the hole, hemostasis was obtained via direct compression with sterile cotton sticks. Collagen gel (2 mg/ml, BD Biosciences, Bedford, Mass.) was placed to the right hole and made the hole full. The hole on left kidney was left blank. The wound was closed in two layers. Mice at 2 weeks and 4 weeks after surgery were sacrificed and the kidneys were harvest for further evaluation.

Multiple Injections

After ischemia reperfusion surgery, collagen gels were injected into the kidney. The collagen gels were injected in the same fashion as described above. The additional injections were performed twice at the interval of 2 weeks from previous injection. All of the rats were sacrificed at 2 weeks after third injection.

Statistical Analysis

Data from the DNA content, cell number, and collagen content assays were analyzed by a single-factor analysis of variance (ANOVA). Differences were considered significant $p<0.05$.

Example 2: Scaffold Implantation

The PGA nonwoven scaffolds consisted of highly porous fiber mesh disks. The 1 retrieved scaffolds at 1, 2, 3 and 4 weeks showed a progressive tissue ingrowth over time. Cell recruitment after implantation was measured by gross morphology and SEM microphotograph. By the fourth week, the implants were completely encapsulated by a connective tissue capsule with abundant host vasculature. Neovascularization was observed in and around the scaffold. Examination of the retrieved implants with scanning electron microscopy (SEM) clearly demonstrated a classic foreign body reaction. The porous scaffold became populated with collagen-producing cells and the interfiber spaces were filled with increasing amounts of collagenous matrix when measured by SEM microphotographs each week after implantation for 4 weeks. Observations after implantation, noted extracellular matrix material gradually filled in 2 the porous architecture of the scaffold.

Example 3: Cellular Component Measurement

Measurement of cell density within the scaffold was achieved by histomorphometry and DNA content analyses (FIG. 1). DNA analysis, performed using a standard extraction kit, confirmed the typical host cellular response. Cell infiltration increased steadily in the first three weeks, followed by a slight decline as matrix production increased by the fourth week. These results were confirmed by histomorphometry, where the average cell counts of representative H&E stained sections showed a similar pattern.

Example 4: Collagen Content Measurement

Figure 2:
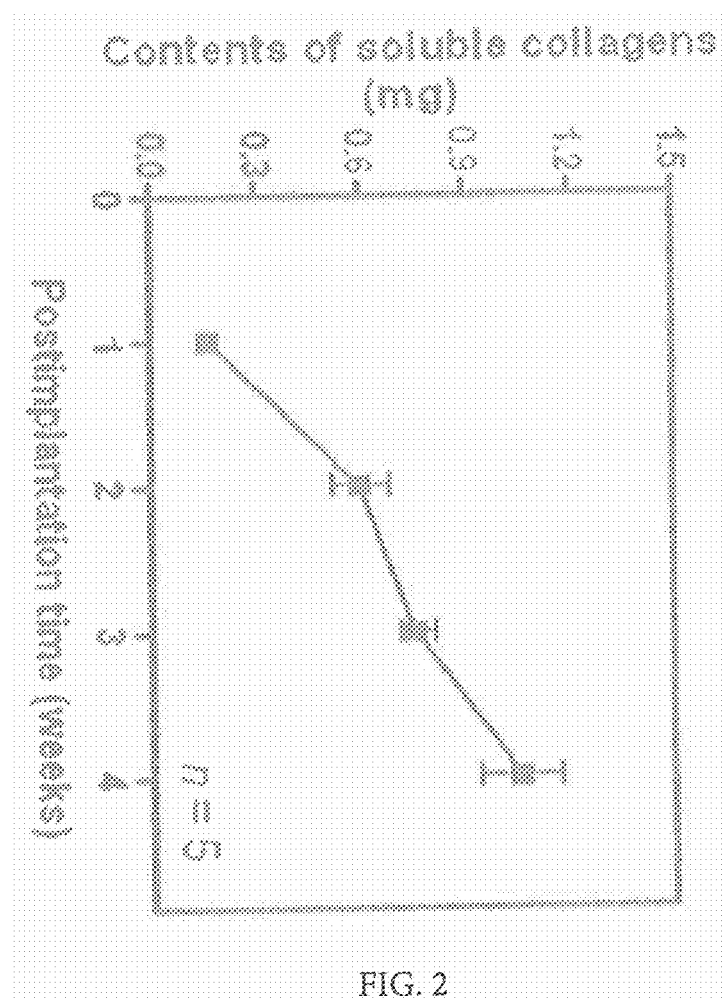
FIG. 2 shows histological evaluation of the implanted scaffolds. Content of soluble collagen. Collagen deposition within the implants gradually increased over time.

Histological analysis of collagen deposition within the scaffolds provided confirmation of the initial SEM images of retrieved implants. Masson's trichrome staining of representative sections after 1, 2, 3, and 4 weeks of implantation showed the gradual buildup of extracellular matrix. The average collagen content of representative tissue samples showed a gradual increase in collagen production by the host cell infiltrate over time (FIG. 2).

Example 5: Characterization of Infiltrating Cells

Figures 3E, 3F, 3G, 3H:
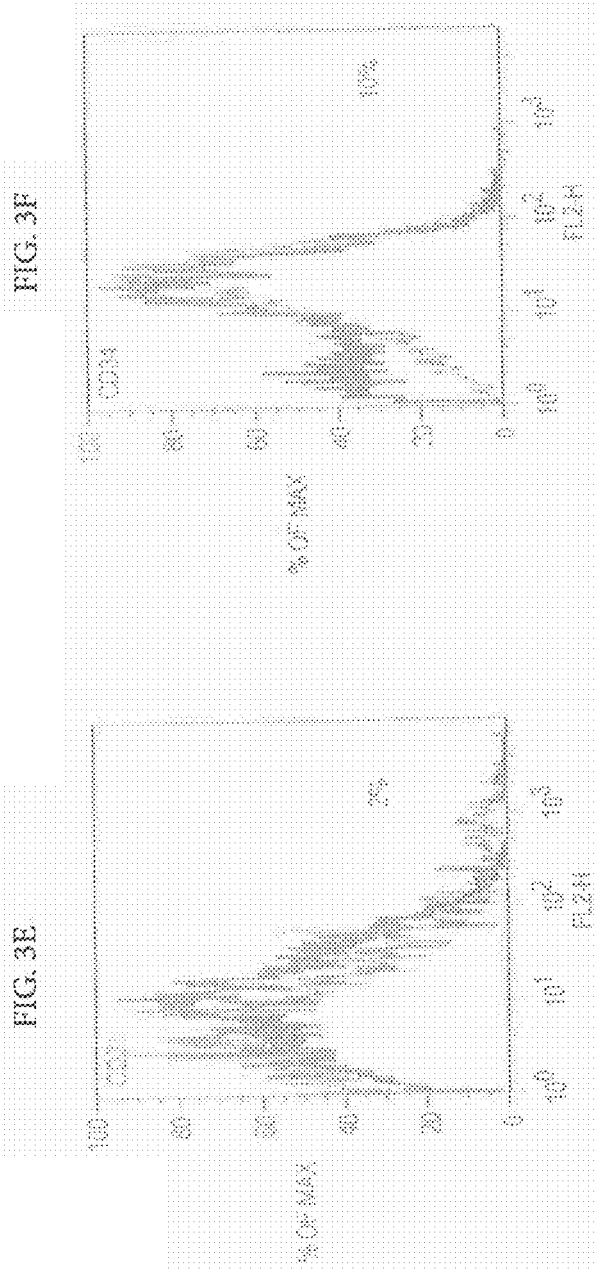

The host cell infiltrate was isolated by standard explant culture isolation methods land the growth of these cells was observed over several passages. The cells grew well in culture and were subcultured with relative ease. Microscopic observations of the cultured cells showed the presence of at least four different cell phenotypes of the infiltrating cells. Flow cytometry was performed for several hematopoietic and mesenchymal stem cell markers, as well as endothelial progenitor cell markers (Sca-1 (FIG. 3A), Flk-1 (FIG. 3B), CD44 (FIG. 3C), CD45 (FIG. 3D), CD31 (FIG. 3E), CD34 (FIG. 3F), CD90 (FIG. 3G) and CD117 (FIG. 3H)). Immunocytochemical staining of cultures of infiltrating cells showed a strong and persistent expression of Sca-1 at all time points and at all passages. However, the expression of mesenchymal stem cell and endothelial progenitor cell markers were absent from these cell populations.

Example 6: Differentiation of Infiltrating Cells (i) Osteogenic Differentiation

Figure 4:
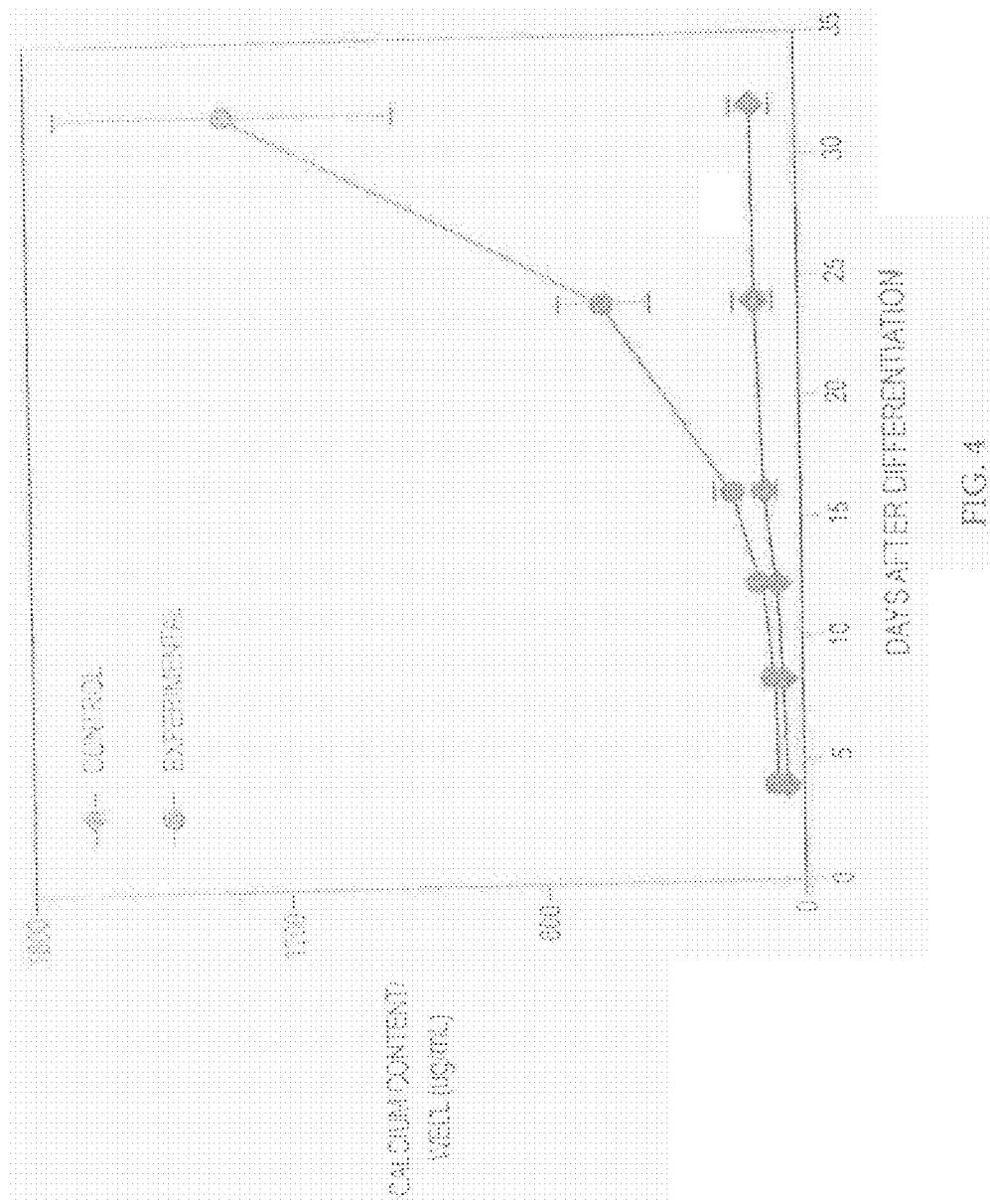
FIG. 4 shows calcification of infiltrating cells under osteogenic conditions. Mineralization of cells was quantified using Alizarin red Assay for calcium. Numbers represent the averages of calcium deposition in culture well. Osteogenic induced cells showed a significant increase of calcium deposition after 16 days of culture.

Recruiting cells were grown in osteogenic-inducing or original culture medium and analyzed using Alizarin Red staining after 4, 8, 16, 24 and 32 days in culture. The cells cultured in osteogenic medium up to 32 days showed an intense Alizarin red staining which indicates calcium deposition. The osteogenic induced cells showed significant mineralization after 16 days. The cells grown in the original culture medium, however, fail to stain for calcium deposition. Quantitative analysis of calcium deposition showed a significant increase after 16 days. The cells demonstrated an approximately thirteen-fold increase in calcium deposition in the osteogenesis-inducing medium compared to cells grown in original culture medium at day 32 (FIG. 4). Von Kossa staining of cells grown in the osteogenic media demonstrated enhanced silver nitrate precipitation by day 16, indicating a high calcium level. The cells grown in original culture medium showed no silver nitrate precipitation over the 16-day period.

Immunocytochemical analysis with osteocalcin antibodies showed a strongly positive expression after 32 days of osteogenic induction.

(ii) Endothelial Differentiation

Infiltrated cells cultured in endothelial EGM showed the typical endothelial differentiation of recruiting cells, "cobblestone" morphology of endothelial cells, after being grown in endothelial-inducing culture medium for 14 days. Immunocytochemical assessment showed strong positive staining for PECAM-1 and von Willebrand factor (vWF). Moreover, the cells formed capillary-like network structures when cultured on Matrigel™. There was no obvious difference observed in the capillary formation regardless of the passage tested. The cells grown in original culture medium showed nophenotypic expression over the 16-day period.

(iii) Adipogenic Differentiation

In vitro incubation of the infiltrating cells in adipogenic media for 16 days induced changes in cellular morphology. The cells lost their original elongated shape and became rounded. After 30 days in culture, the cytoplasm had completely filled with vacuoles that stained positively with Oil-Red-O, a common stain for lipid accumulation, which indicates an adipose-like phenotype. The cells grown in original culture medium showed no lipid accumulation over the 30-day period.

(iv) Myogenic Differentiation

Treatment of the cells with 5-azacytidine for 24 hr followed by incubation in myogenic media induced fusion of the cells to yield multinucleated clusters detected by phase contrast microscopy. The fused cells formed myofiber-like structures after 16 days in myogenic medium. Immunocytochemistry showed strong positive expression for a-smooth muscle actin and desmin after 16 days in culture. The cells grown in original culture medium showed no myogenic expression over the 16-day period.

Example 7: Dexamethasone-Incorporated PGA Scaffolds

Figure 5A:
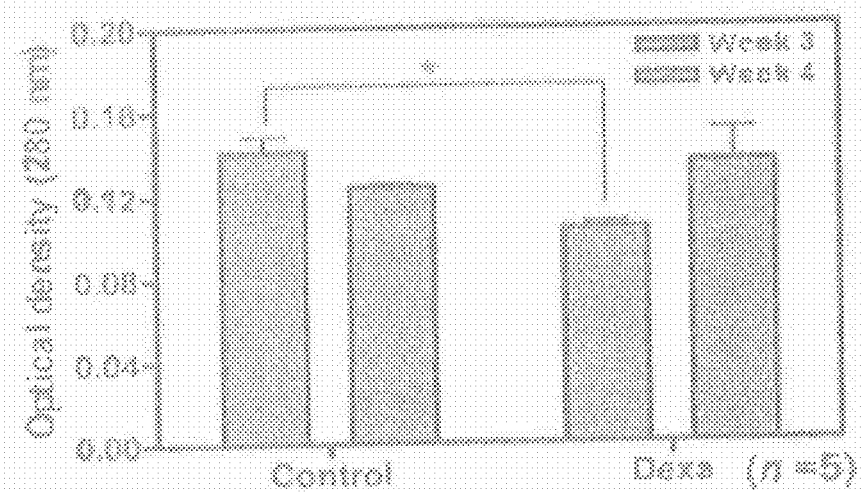
FIG. 5 shows dexamethanson-incorporated PGA scaffolds; (A) DNA content in the implanted scaffolds ($P<0.05$). (B) Contents of soluble collagens in the implanted scaffolds ($P<0.05$).
Figure 5B:
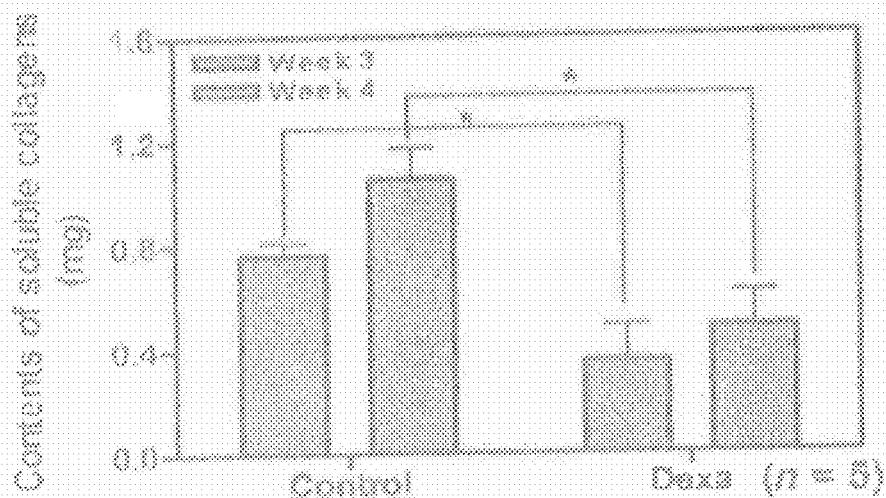

Measurement of cellular components within the dexamethasone-incorporated PGA scaffolds was accomplished by DNA content measurement. Cellularity within the control scaffolds were slightly declined at 4 weeks after implantation. However dexamethasone-incorporated PGA scaffolds showed a gradual increase in DNA content by the same time point (FIG. 5A). Interestingly, collagen content within the dexamethasone-incorporated PGA scaffolds was significantly reduced as compared to the control scaffolds ($P<0.05$) (FIG. 5B).

Example 8: Regeneration Potential of Renal Tissue Using Injectable Hydrogels

Various gel scaffolds including collagen based gel scaffolds, and other biomaterials, including collagen type I, collagen based kidney tissue gel matrix, synthetic gel matrix and keratin based gel matrix were tested in regeneration of kidney tissues. The results of all injections demonstrated similar findings with formation of glomerular and tubular structures. Thus, stem cells or progenitor cells can be recruited to target specific sites, and corresponding cells and tissues are formed.

Following injection, the kidneys were evaluated at various time points (1, 2, 3, 4, 6, 9 and 12 weeks after injection) using histological staining, H&E staining, and Masson's Trichrome staining. The following immunohistochemical stainings were used to evaluate the kidneys following injection: BrdU cell tracing for detection of the recruiting host cells; vascular endothelial cells (Factor VIII or CD31); Podocytes: Synaptopotin; Proximal tubular cells: Aquaporin 14; Tubular cells: Cytokeratin; Proliferating cell nuclear antigen (PCNA) staining; and Stem/progenitor cell markers (CD34, CD44, CD45, CD90, CD105, CD133, Flk-1, Sca-1).

Figure 6:
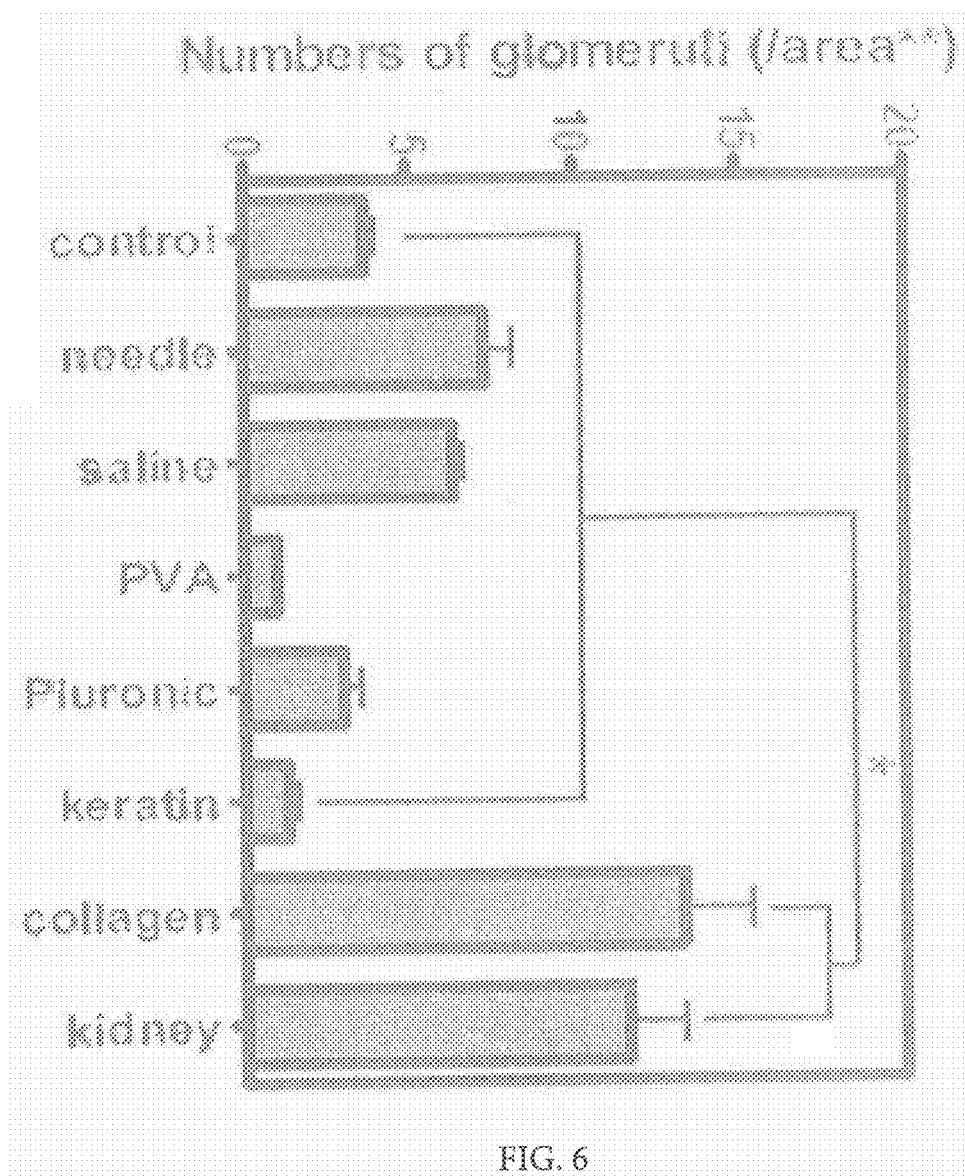
FIG. 6 is a graph showing the numbers of glomeruli in the injured area at week 2 after hydrogel injection (based on ×100 magnification of PCNA staining, *$P<0.05$, **area=0.57 $mm^2$).

Histological images at 2 weeks after collagen hydrogel injection identified glomerular structures and tubular structures in the injured area: Likewise, histological images each week for 4 weeks after kidney-derived hydrogel injection identified glomeruli in the injured area. FIG. 6 is a graph showing the numbers of glomeruli in the injured area at week 2 after hydrogel injection (based on ×100 magnification of PCNA staining, *$P<0.05$, **area=0.57 mm$^2$). Counting of glomerular structure was done with anti-PCNA staining.

Example 9: Regeneration Potential in the Renal Disease Mouse Model Using an Injectable Collagen Hydrogel In the tissue regeneration study, injection of gel scaffolds into kidney parenchyma resulted in multiple glomerular and tubular structure formation by 1 week and continued to mature with time. Presence of red blood cells was observed within the glomeruli, which is confined in the Bowman's capsule. The cells consisting of the newly formed renal structures expressed BrdU and proliferative cell nucleus antigen, which indicate dividing and proliferating cells. These observations suggest that the renal structures found within the injected site are regenerated tissues. Glomerular-endothelial and tubular structures were confirmed using CD31 and Cytokeratin antibodies.

In this example, CBA/J inbred mice, an art recognized renal disease model showing renal tubulointerstitial lesions, was used. CBA/J inbred mice are widely used as a general purpose strain. CBA/J strain is the only CBA substrain that carries the Pde6b$^{rd1}$ mutation, which causes blindness by wean age. The CBA/J inbred mouse strain is used to study granulomatous experimental autoimmune thyroiditis (G-EAT), is relatively resistant to diet-induced atherosclerosis, and develops a mild hearing loss late in life, with most of the hearing loss occurring in the higher frequencies. Renal tubulointerstitial lesions have been observed in this strain at a high frequency. Some CBA/J mice spontaneously develop exocrine pancreatic insufficiency syndrome with a high frequency of renal tubulointerstitial lesions in a disease mouse model (CBA/J mouse, Jackson Lab.).

Figure 7:
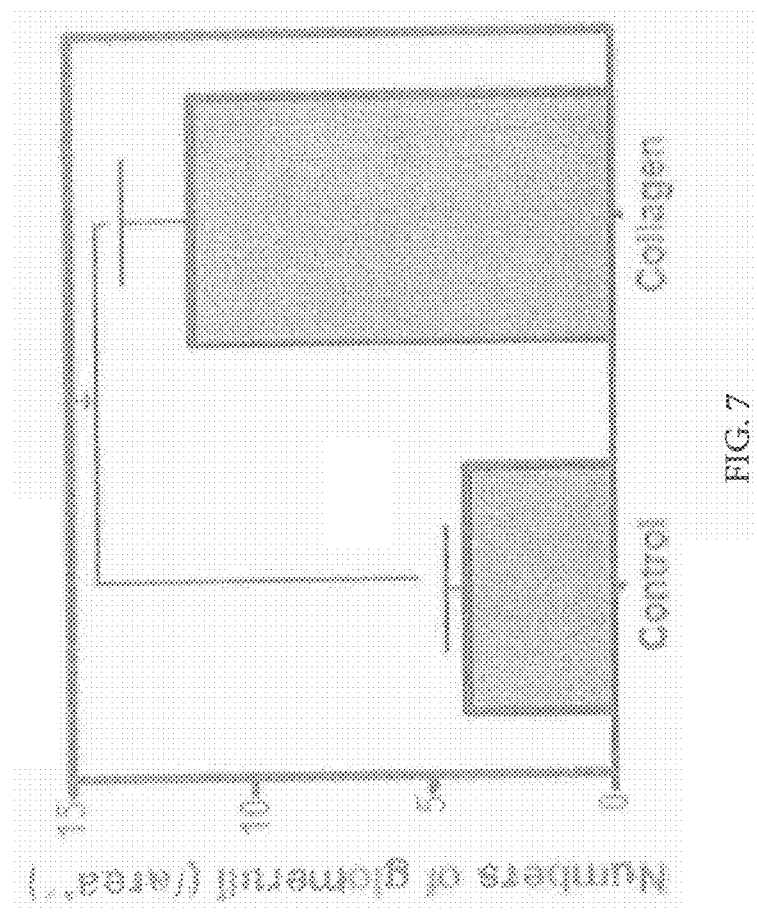
FIG. 7 is a graph showing the number of glomeruli in the injured area at week 22 after hydrogel injection (based on ×100 magnification of PCNA staining, *$P<0.05$, **area=0.57 $mm^2$).

Two experimental groups were compared (saline injection (0.9% sodium chloride, Abbott Laboratories) control, and rat tail type I collagen (3.5 mg/mL, BD Biosciences)) at 1, 2, 3, and 4 weeks after injection using histological staining, H&E staining, and Masson's Trichrome staining. The following immunohistochemical staining was used to evaluate the injured area in the kidneys at 1, 2, and 4 weeks after collagen hydrogel following injection: BrdU cell tracing for detection of the recruiting host cells; vascular endothelial cells (Factor VIII or CD31); Podocytes: Synaptopotin; Proximal tubular cells: Aquaporin ½; Tubular cells: Cytokeratin; Proliferating cell nuclear antigen (PCNA) staining; and stem/progenitor cell markers (CD34, CD44, CD45, CD90, CD105, CD133, Flk-1, Sca-1). FIG. 7 is a graph showing the number of glomeruli in the injured area at week 2 after hydrogel injection (based on ×100 magnification of PCNA staining, *P<0.05, **area=0.57 mm$^2$). Collagen injection more than doubled the number of glomeruli compared to the saline control. Counting of glomerular structure was done with anti-PCNA staining.

In addition, a rat renal insufficiency model was created to test whether regeneration occurs in the diseased kidney. Lewis rats (male) were used. Renal insufficiency was induced by ligation of the renal artery and vein for 60 min. Characterization was done (BUN/Cr and histology). Injection of collagen into the pathologic kidney showed regeneration of kidney tissues as demonstrated by H&E staining, and immunohistochemistry staining for CD44 and PCNA.

Example 10: Sustained Pressure Needed for Renal Tissue Regeneration

Figure 8B:
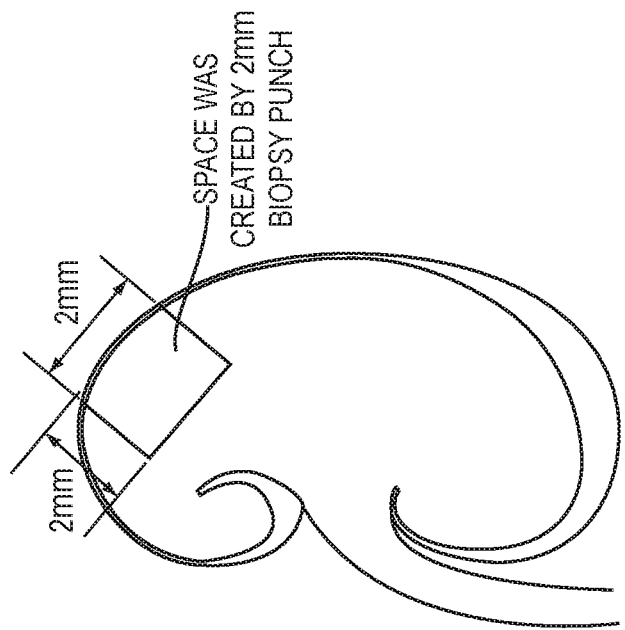
FIG. 8B shows a schematic of the space created in the kidney by a 2 mm biopsy punch.
Figure 8A:
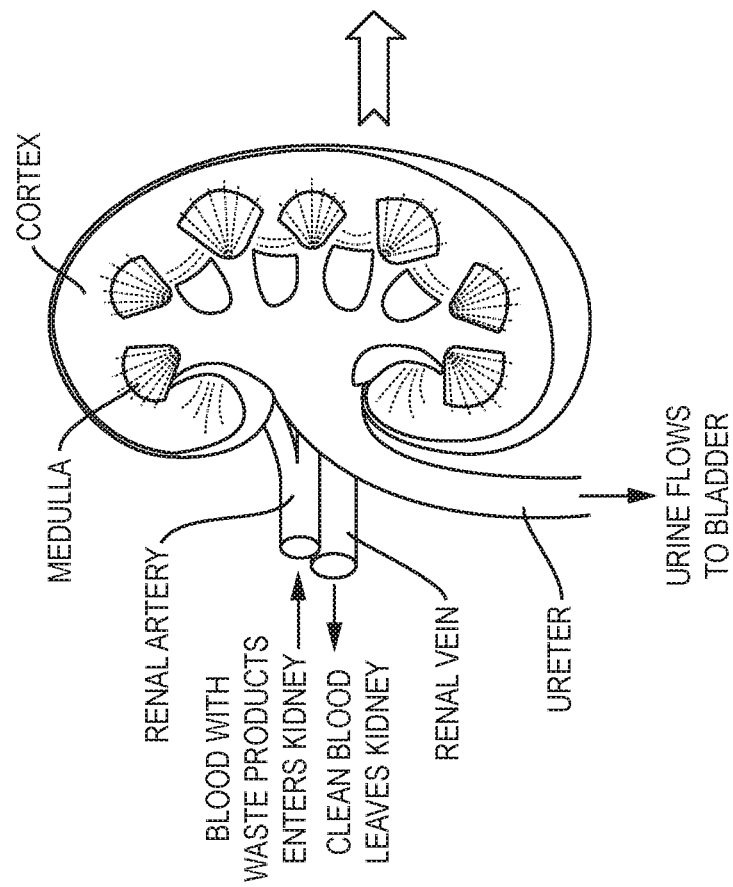
FIG. 8A shows a schematic of the CD1 mouse model kidney.
Figure 9:
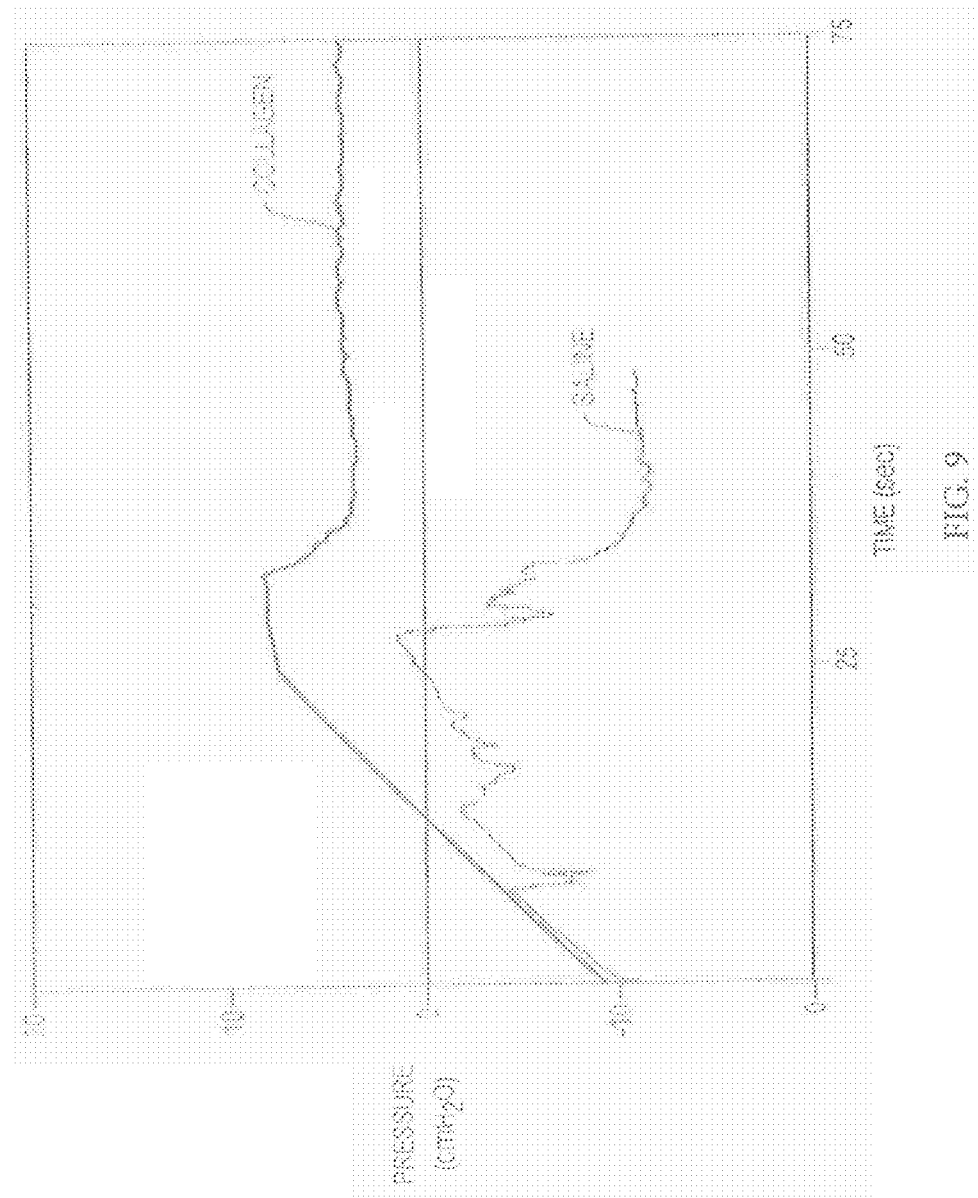
FIG. 9A is a graph comparing the pressure within the kidney following injection of 2 mg/ml collagen solution versus time and FIG. 9B is a similar graph comparing pressure within the kidney following injection of saline versus time.

To determine whether regeneration of kidney structures is due to the created space, pressure or both, space was created surgically within the renal cortex without pressure. FIG. 8A shows a schematic of the CD1 mouse model kidney. FIG. 8B shows a schematic of the space created in the kidney by a 2 mm biopsy punch. A 2 mm biopsy punch was created in a mouse kidney. Collagen injected into the surgically created space in the renal cortex showed no evidence of renal structure or cortex formation, indicating that pressure is necessary to initiate the regenerative process. Provision of space without pressure showed the formation of adipose-like tissues when analyzed by immunohistochemical staining in the injured area at week 2 after formation of the surgically created space. FIG. 9 is a graph comparing the pressure within the kidney following injection of (a) 2 mg/ml collagen and (b) saline versus time. Table 1 shows the pressure measurement within the kidney after injection.

TABLE 1

Pressure measurement within the kidney following injection.

| | Maximum Pressure (cmH$_2$O) | Sustained Pressure (cmH$_2$O) |
|---|---|---|
| Collagen | 18.6 ± 3.3 | 13.3 ± 4.9 |
| Saline | 15.9 ± 1.5 | 0.5 ± 0.5* |

*Lewis Rats (n = 3),
*P < 0.05

Figure 10:
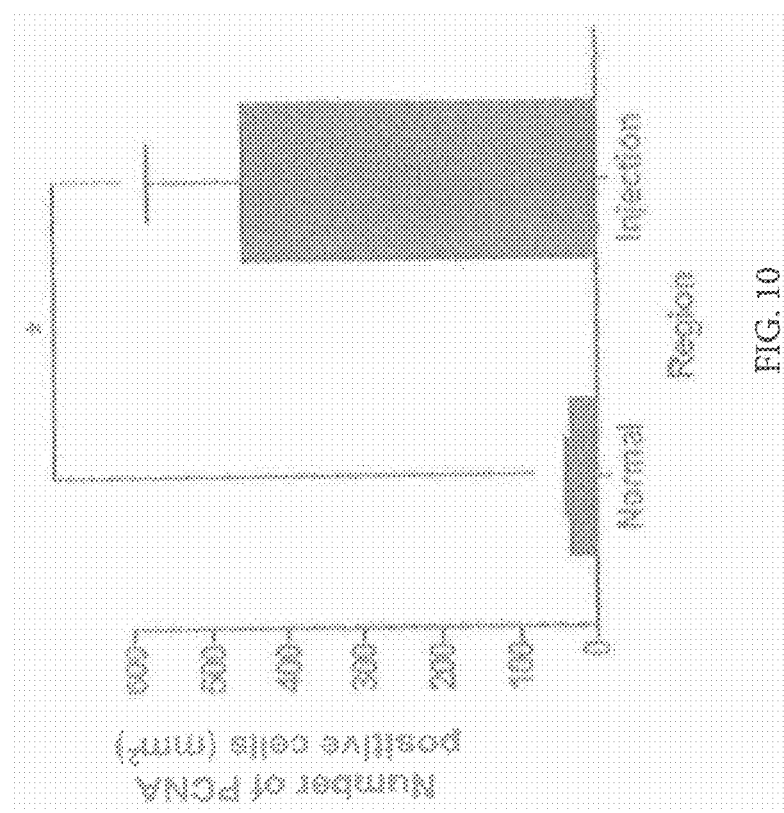
FIG. 10 is a graph that depicts the number of PCNA-positive cells in the normal and injection regions after 2 week injection (*$P<0.01$).

Example 11: Characterization of Infiltrating Host Cells and Renal Tissue Regeneration in the Normal Mouse Kidney Neutralized collagen gels (0.2% wt/vol) were injected into the kidneys of normal CD1 mice. Saline injections and needle sticks without injection of material were also performed as controls. At 2 weeks after injection, each kidney contained inflammatory and fibroblastic cells in the injected regions. However, in the collagen group, a higher number of newly formed glomerular-like structures was seen residing in the injected collagen when compared to the other groups. In order to detect host cells that had infiltrated into the injection regions of the kidney, we examined the localization of cells positive for PCNA, which is expressed particularly in the early G1 and S phases of the cell cycle and is a marker for proliferating cells. Kidneys injected with collagen contained a large PCNA-positive cell population and showed progressive renal tissue formation in the injected regions over time. The number of PCNA-positive cells in the injected regions was significantly higher than in normal regions (P<0.01, FIG. 10). This indicates that host cells could migrate from other areas into the injected regions. Interestingly, it seems that these host cells (PCNA-positive) contribute to the formation of renal structures, especially the high number of glomeruli that were observed in the injected regions in collagen treated animals.

Figure 11:
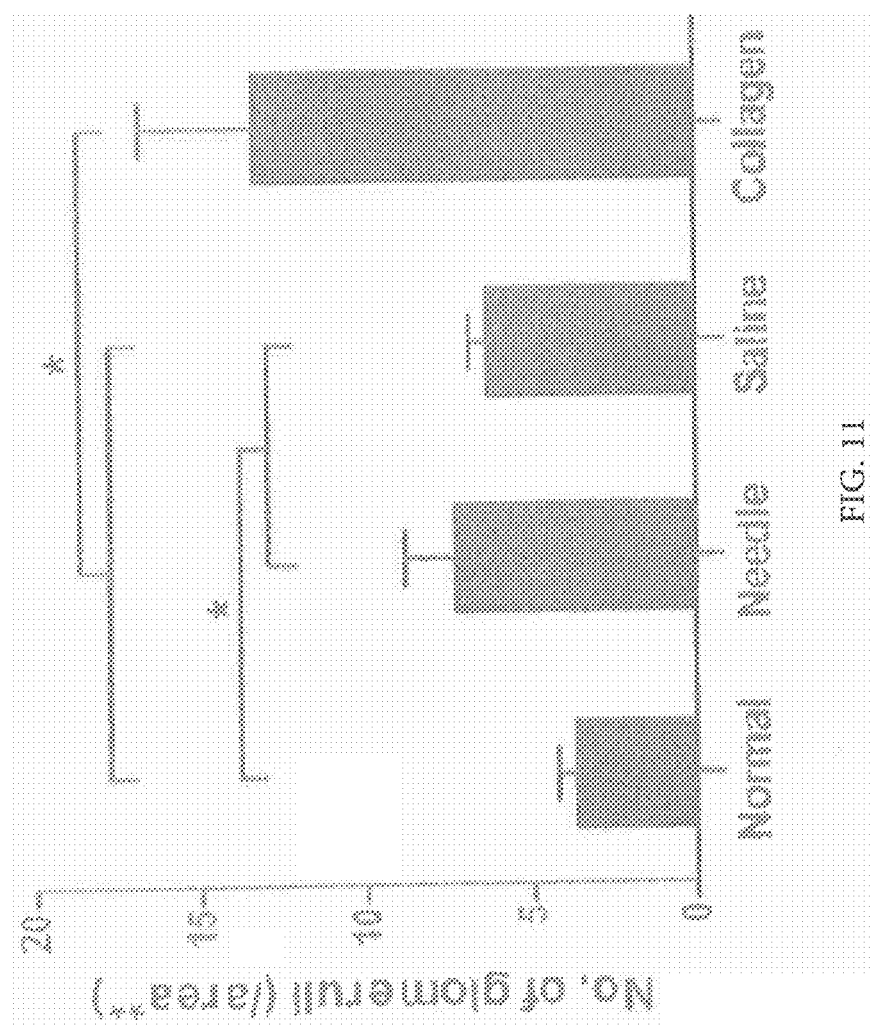
FIG. 11 is a graph that depicts the quantitative analysis of number of glomeruli per area in the normal CD1 mouse kidneys after injection (*$P<0.05$).

To determine if the cells that infiltrated the collagen biomaterial were host renal stem/progenitor cells, immunohistochemistry for CD24, CD44, and CD 133 was performed. We found that a population of host cells expressing PAX-2, CD24, CD133 and CD44 was able to infiltrate the injection regions of both normal mice and rats with renal ischemia/reperfusion injury. The infiltrating host cells present within the injected regions of these kidneys expressed both renal stem/progenitor cell markers, CD24 and CD133, as well as the mesenchymal stem cell marker, CD44. We observed the presence of CD44$^+$ cells in the injected regions after collagen gel injection. The CD44$^+$ cells were localized within the tubular area and at the glomerular level within the parietal layer of Bowman's capsule. However, we did not observe CD44+ cells in the normal regions of the same kidney. In addition, the regenerated renal structures were identified by immunohistochemistry with renal cell specific markers. The glomerular-like structure expressed synaptopodin and CD31 and tubular-like structure expressed cytokeratin in a manner nearly identical to that of glomeruli and tubules in native kidney tissue. In fact, the number of glomeruli found in the collagen gel regions was significantly higher compared to native kidney tissue regions and the other groups (P<0.05, FIG. 11). Moreover, it seems that these cells contribute to the development of new renal tissue structure. These cells proliferate and eventually re-differentiate into typical renal cells during the regenerative process.

Example 12: Renal Ischemia/Reperfusion Rat Model

All of the animals undergoing renal ischemia and reperfusion procedures survived at least 3 weeks after injury. At 2 weeks after the surgery, the kidney samples were retrieved and analyzed. The ischemic kidneys showed tubular dilation and brush border loss as well as intratubular cast formation and degeneration of tubular architecture. Some tubular structures became edematous and necrotic. The number of glomeruli decreased in the injured kidneys, and some swelled and developed sclerosis. After ischemia/reperfusion injury was confirmed, the collagen gels were injected directly into the ischemic kidneys. The injected regions could be easily identified, as most showed the presence of increased interstitial leukocytes and other infiltrating cells.

Newly formed glomerular-like structures and tubular-like structures were observed at 2 weeks after the collagen injection. PCNA-positive cells in the injected regions were increased. To characterize the phenotype of the newly formed structures, we examined the expression of the renal cell markers, synaptopodin and CD31. In addition, the tubular structure stained positive for neprilysin.

To identify the host cells present in the injected regions, immunohistochemistry for the specific renal stem/progenitor cell markers was performed. Immunohistochemistry of the collagen injection regions from ischemic kidneys revealed that CD24, a marker of the renal embryonic progenitor cells, was expressed. In the injection regions, we observed the presence of $CD133^+$ and $CD24^+$ cells of the interstitial and tubular structures. The $CD44^+$ and $PAX-2^+$ cells were identified not only in the interstitial and tubular structure, but also at the glomerular level within the parietal layer of Bowman's capsule in the injection area. These cells were rarely found in the native kidney tissue outside the injection regions.

Figures 12A, 12B:
FIGS. 12A-B are graphs that show the quantitative analysis of number of glomeruli in the injection regions of the renal ischemia/reperfusion rats.

After ischemic injury, the number of glomeruli in the native tissue was significantly decreased ($7.9\pm0.35/mm^2$, $4.02\pm0.18/mm^2$, and $3.29\pm0.186/mm^2$; normal kidney, 2 weeks, and 4 weeks after surgery, respectively; $P<0.0001$). However, in the collagen injection group, the number of glomeruli was significantly increased in the injected regions compared to native regions with ischemic injury ($11.44\pm0.72/mm^2$ vs. $4.02\pm0.18/mm^2$; $12.08\pm1.2/mm^2$ vs. $3.29\pm0.186/mm^2$; 2 weeks and 4 weeks; $P<0.01$). Interestingly, the density of the glomeruli was higher within the collagen biomaterial than in normal kidney (FIGS. 12A-B).

Figure 13:
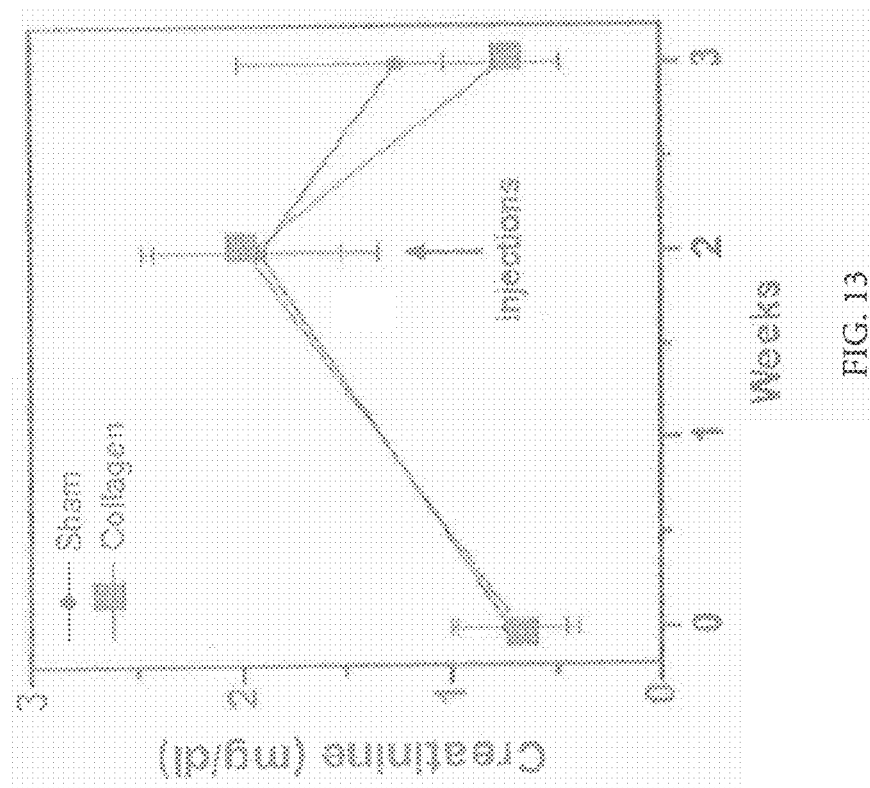
FIG. 13 is a graph that shows the blood serum analysis of creatinine levels for functional evaluation of the ischemic injured kidneys.

In order to determine whether the newly formed glomeruli and tubules could contribute to functional recovery of the kidney, blood samples were analyzed for creatinine levels. One week after the injections, renal function improved in all experimental groups (blood serum creatinine level; $1.26\pm0.29$ mg/dl in the sham; $0.93\pm0.16$ mg/dl in the saline group, and $0.76\pm0.1$ mg/dl in the collagen group). Though there was no significant difference in the three groups, there was a trend indicating that collagen injection led to the most improvement in renal function, while the sham group had the least (FIG. 13).

Figure 14A:
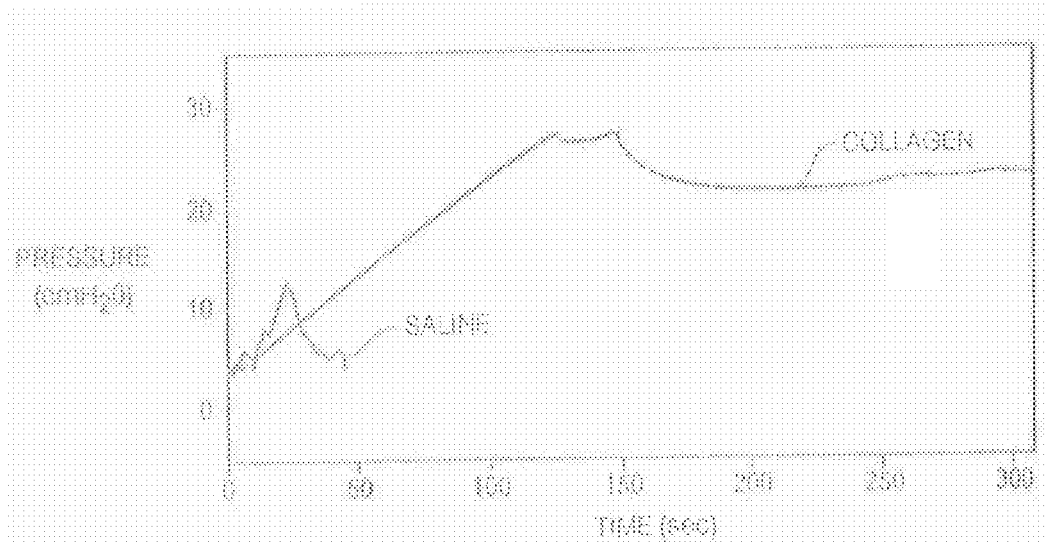
FIGS. 14A and 14B are graphs showing measurements of a partial pressure in the injection regions after injection.
Figure 14B:
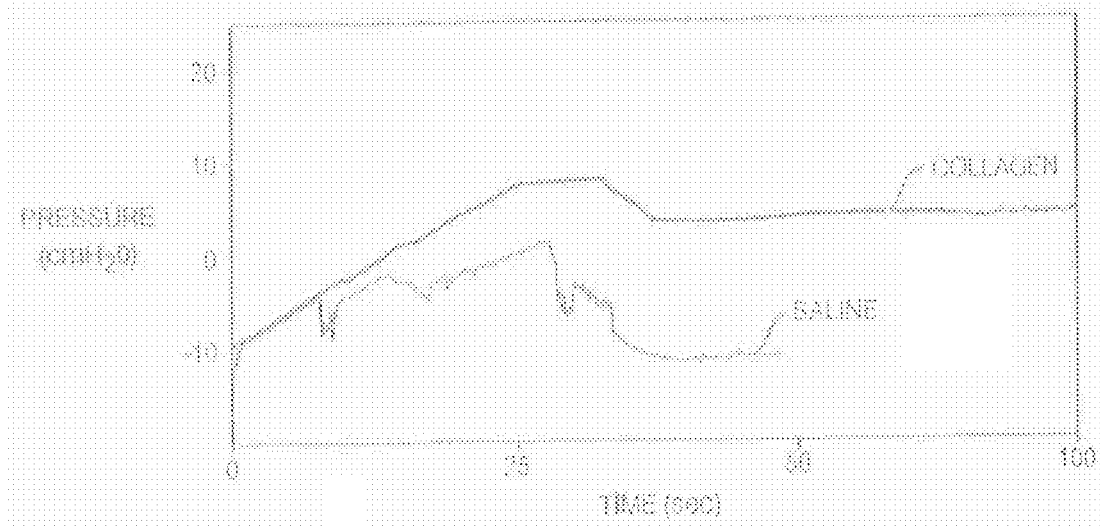
Figure 15:
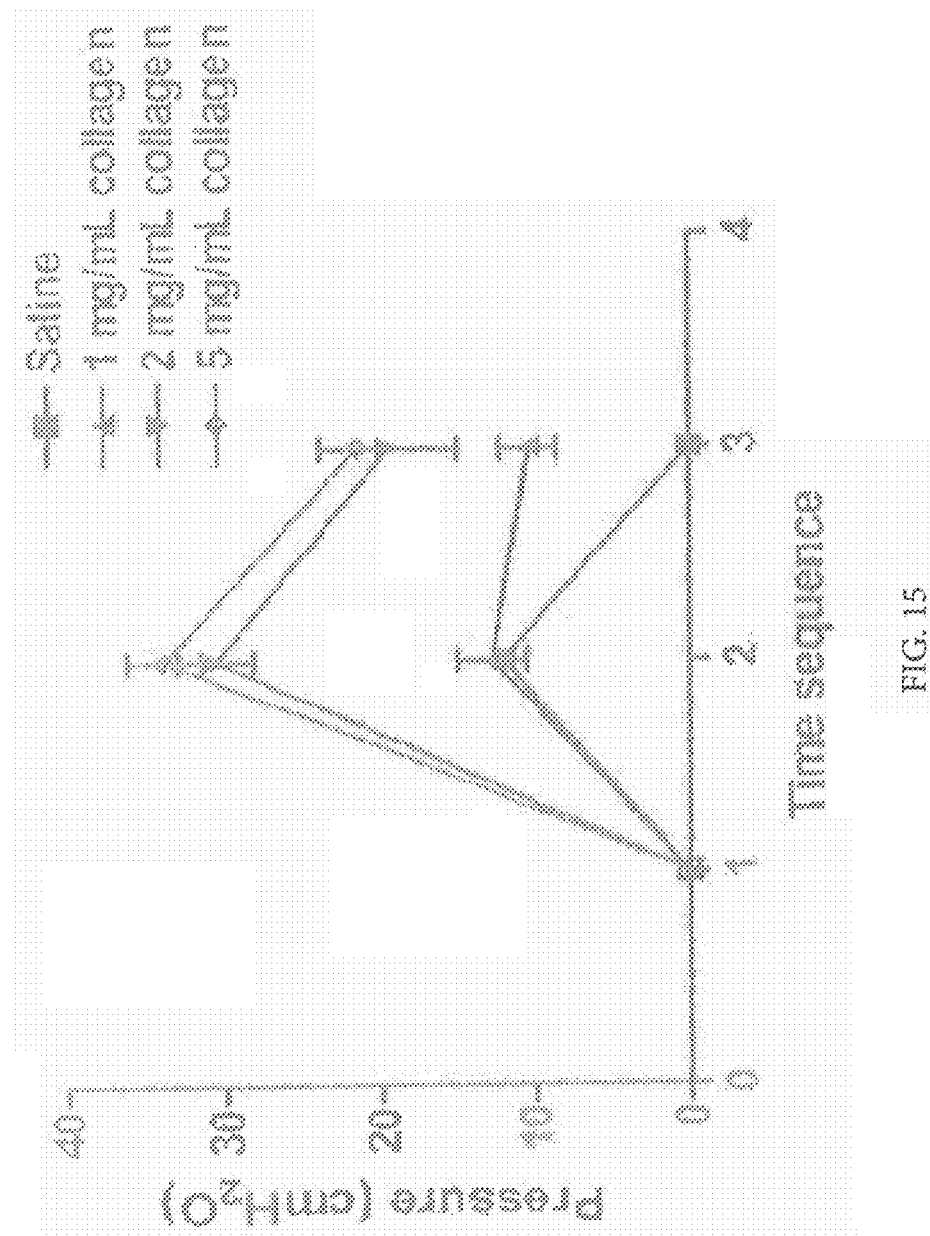
FIG. 15 shows measurement of a partial pressure in the injection regions after collagen injection with different concentrations in mice.

Example 13: Positive Pressure Measurement During the Injection and Number of Glomeruli after Injection The positive pressure in the injection regions of the kidney was measured after saline and collagen injections. After saline injection, the pressure surged in seconds and returned to baseline quickly. In the collagen groups, the pressure gradually increased to a peak then maintained over 70% of the ultimate pressure. The 2 mg/mL and 5 mg/mL concentrations had higher peaks and sustained pressure as compared with saline and 1 mg/mL collagen, while there was no difference between 2 mg/mL and 5 mg/mL groups (FIGS. 14 and 15). We assume that the collagen gels induce partial damage in the kidney as well as provide a mechanical stimulus caused by positive pressure With regards to a biopsy punch injury, we made a specific defect extended from cortex to medulla. At 2 weeks after injury, renal regeneration was observed in either collagen-filled or blank kidneys. The collagen group maintained the initial shape of the kidney, however the control group collapsed. Histologically, numerous newly formed glomeruli were observed in the collagen group. In addition, the space provided by the biopsy punch may accommodate the recruited cells and allow differentiation into required lineages to participate in tissue/organ repair and regeneration.

Total number of glomeruli in the whole kidney section was decreased after ischemia injury ($283.2\pm6.40$ vs. $171.9\pm4.88$, $p<0.0001$). After an initial or multiple collagen injections, the total number of glomeruli increased compared to ischemia-injured kidney ($p=0.001$). However, there was no difference between 1st, 2nd, and 3rd injections (FIG. 16).

The invention claimed is:

1. A method of kidney regeneration comprising:
   injecting a substantially cell-free biocompatible substance comprising collagen under pressure into a target site in a kidney to create a hyperbaric environment at the target site;
   maintaining positive pressure in a range of about 5 cm $H_2O$ to about 70 cm $H_2O$ at the target site for at least one hour due to the viscosity of the substance or collagen swelling-during which time the hyperbaric environment recruits tissue-specific progenitor cells to the target site; and
   wherein the tissue-specific progenitor cells recruited to the target site undergo differentiation to produce new glomeruli structures within the kidney.

2. The method of claim 1, wherein the biocompatible and biodegradable substance-further comprises a substantially cell-free polymeric biocompatible and biodegradable collagen substance.

3. The method of claim 2, wherein the collagen biocompatible and biodegradable substance is a collagen solution having a collagen concentration from about 2 mg/mL to about 5 mg/mL.

4. The method of claim 3, wherein the collagen solution thermogels at body temperature and the step of delivering the biocompatible and biodegradable substance further comprises injecting the collagen solution in a chilled state as a liquid and the step of maintaining positive pressure at the target site further comprises gelling the substance following injection.

5. The method of claim 1, wherein the biocompatible and biodegradable substance further comprises a hydrogel.

6. The method of claim 3, wherein the step of delivering the collagen solution into the target site comprises injecting the substance into the target site and monitoring an injection pressure such that a hyperbaric environment is attained at the target site.

7. The method of claim 1, wherein the step of delivering the biocompatible substance into the target site comprises surgically implanting the substance at the target site.

* * * * *